United States Patent
Bar

[19]

[11] Patent Number: 6,165,142
[45] Date of Patent: Dec. 26, 2000

[54] BIOMEDICAL APPARATUS

[75] Inventor: Christopher A. Bar, Belleville, Ill.

[73] Assignee: Roho, Inc., Belleville, Ill.

[21] Appl. No.: 09/158,351

[22] Filed: Sep. 21, 1998

[51] Int. Cl.$^7$ .................................................. A61B 5/00
[52] U.S. Cl. ............................................................ 600/595
[58] Field of Search .................................. 600/587, 592, 600/595

[56] References Cited

U.S. PATENT DOCUMENTS

| | | |
|---|---|---|
| Re. 28,754 | 3/1976 | Cook et al. . |
| 2,558,805 | 7/1951 | Yaglou . |
| 3,056,005 | 9/1962 | Larson . |
| 3,533,095 | 10/1970 | Collins . |
| 3,631,438 | 12/1971 | Lewin . |
| 3,718,791 | 2/1973 | Szablowski . |
| 3,860,773 | 1/1975 | Fontaine . |
| 4,020,482 | 4/1977 | Feldl . |
| 4,068,334 | 1/1978 | Randall . |
| 4,086,458 | 4/1978 | Dickey . |
| 4,137,116 | 1/1979 | Miller . |
| 4,172,216 | 10/1979 | O'Shea . |
| 4,220,815 | 9/1980 | Gibson et al. . |
| 4,401,896 | 8/1983 | Fowler et al. . |
| 4,426,884 | 1/1984 | Polchaninoff . |
| 4,471,177 | 9/1984 | Doughty . |
| 4,497,989 | 2/1985 | Miller . |
| 4,503,705 | 3/1985 | Polchaninoff . |
| 4,551,713 | 11/1985 | Aossey . |
| 4,565,910 | 1/1986 | Musick et al. . |
| 4,617,433 | 10/1986 | Hoshikawa et al. . |
| 4,638,307 | 1/1987 | Swartout . |
| 4,644,801 | 2/1987 | Kustanovich . |
| 4,827,763 | 5/1989 | Bourland et al. . |
| 4,833,457 | 5/1989 | Graebe, Jr. . |
| 4,845,323 | 7/1989 | Beggs . |
| 4,876,419 | 10/1989 | Lodini . |
| 5,068,504 | 11/1991 | Rogers . |
| 5,113,176 | 5/1992 | Harris . |
| 5,471,405 | 11/1995 | Marsh ...................................... 600/592 |
| 5,813,142 | 9/1998 | Demon ..................................... 600/592 |

*Primary Examiner*—Max Hindenburg
*Attorney, Agent, or Firm*—Polster, Lieder, Woodruff & Lucchesi, L.C.

[57] ABSTRACT

A biomedical apparatus for monitoring and evaluating physical properties associated with a biologic or biomedical system is provided. When adapted to monitor and evaluate pressure at any interface between two abutting surfaces, the biomedical apparatus includes a sensor pad including at least one pressure sensor that is adapted to be disposed between the two surfaces to measure pressures exerted on one surface by the other surface, and generate data representative of measured pressures. At least one transducer is provided, with one transducer being in communication with each sensor for generating output signals representative of pressures measured by the sensor. Electronic circuitry further is provided that includes data processing circuitry for processing output signals generated by the transducer and generating pressure data based upon pressures measured by the sensor. A display is electrically connected to the data processing circuitry for visually displaying information representative of pressure data generated by the data processing circuitry. The electronic circuitry and transducers are disposed in a hand-held housing, and the display is mounted on the housing. Tubing extending between the sensor pad and the housing connects each sensor to one transducer. A power source disposed inside the housing for supplying power to the electronic circuitry. In the preferred embodiment, three hydraulic pressure sensors having quadfoliate configurations are arranged on the sensor pad to provide sufficient surface area to cover a bony prominence of an individual resting against a surface.

57 Claims, 17 Drawing Sheets

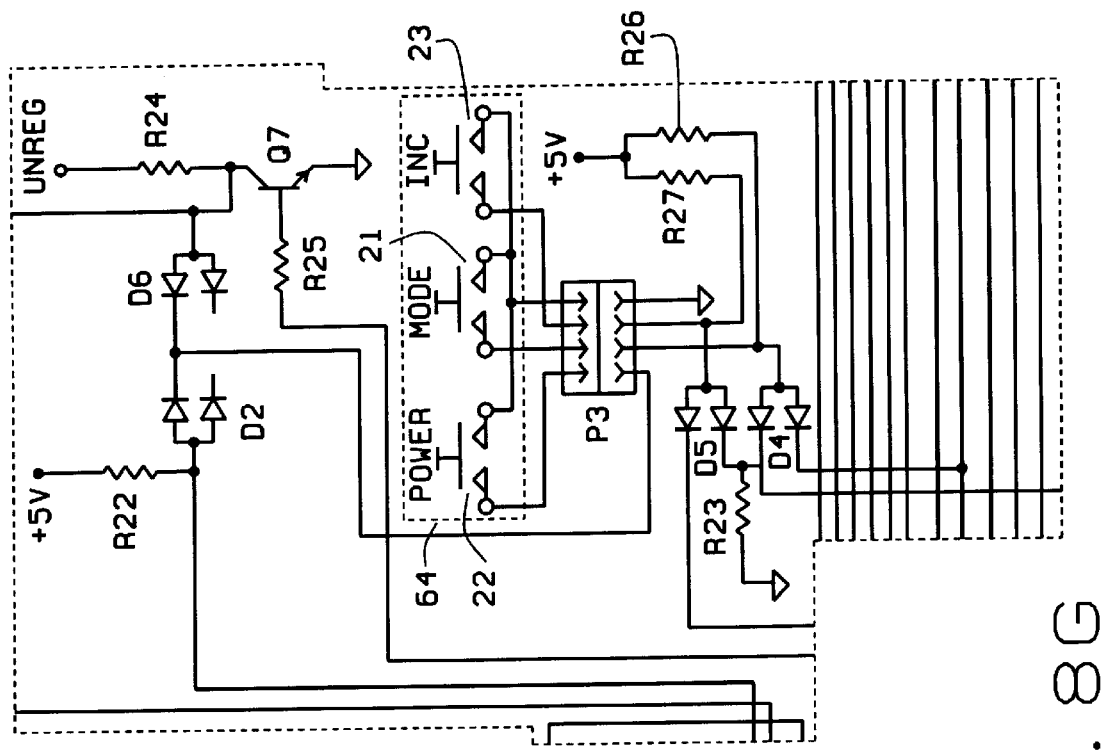
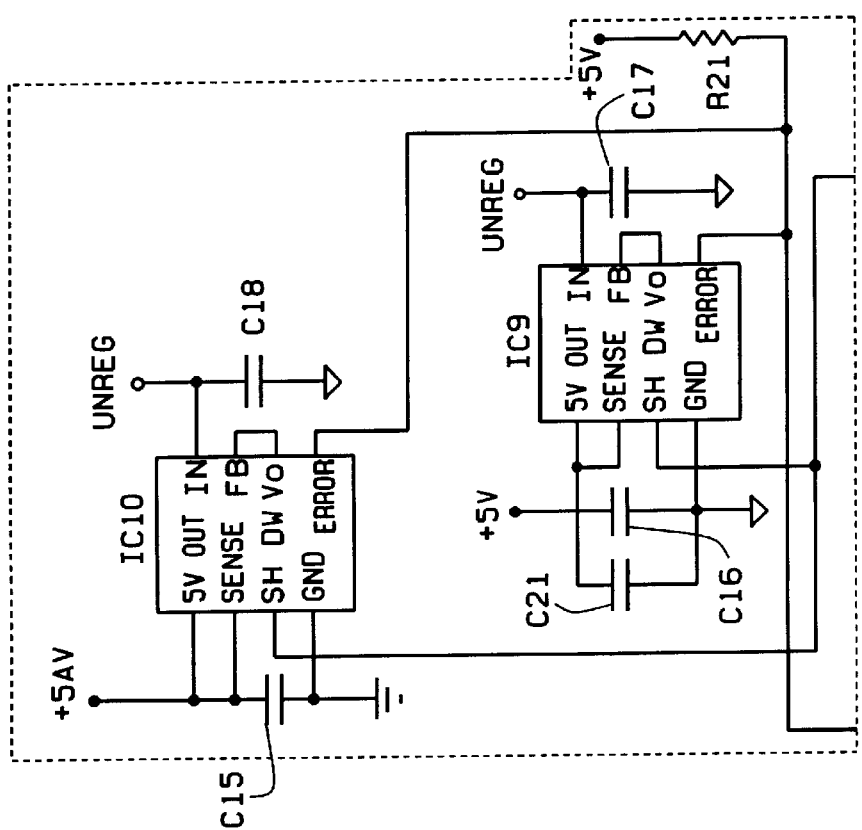
FIG. 8G
FIG. 8F

BIOMEDICAL APPARATUS

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to biomedical instrumentation systems typically used in biomedical research and patient care applications, and more specifically to a biomedical apparatus for measuring and evaluating physical variables associated with biologic or biomedical systems such as, for example, pressure, temperature, partial pressure oxygen ($PO_2$), carbon dioxide ($CO_2$), humidity, friction, force (weight and mass), displacement (linear and angular), radiant energy (optical) or blood flow. The present invention includes at least one biomedical or physical sensor that measures physical variables, at least one transducer that generates electrical signals representative of the measured physical variables, electronic circuitry for processing and evaluating signals generated by the transducer, and a display assembly for providing information based upon the physical properties exhibited by the biomedical system. The discussion of the preferred embodiment of the present invention sets forth a biomedical apparatus that is adapted to measure pressure at any interface between two surfaces to determine and evaluate physical stresses. For example, the apparatus can be used to measure pressure at an interface between an individual's body and a support surface such as a mattress to determine and evaluate physical stresses exerted on the body. However, it will be appreciated that the present invention can be readily adapted to monitor and evaluate a wide range of physical properties such as those listed above by employing appropriate physical sensors and transducers to measure the desired physical properties.

Pressure sores, also referred to as decubitus ulcers, bed sores and trophic ulcers, are a traumatic condition that often appear on the body of individuals who are disabled or neurologically impaired. One of the primary factors contributing to the formation of pressure sores is tissue deformation which causes occlusion of blood flow. Tissue deformation itself is difficult to measure, but it can be evaluated by examining the principle forces of pressure, shear and friction which act together to distort and deform the tissues. When these forces are unevenly distributed over an area of the body, the tissues deform and distort, which, in turn, may produce severe or prolonged circulatory interference through the collapse of the vascular beds.

When sitting or lying on a surface, the underlying skeletal structure provides an anvil against which the soft tissues can be compressed and deformed. Where the tissues are in a relatively thin state, for example, over the bony prominences of the body, the ability to relieve pressure by dissipation in the tissues is noticeably reduced. Therefore, bony prominences that are sparsely covered by only a thin layer of tissue are highly vulnerable to harmful pressure. Uneven pressure distribution also causes internal shearing effects that are hazardous to living cells. Deformation of tissues caused by shearing forces can occur wherever friction exists between the skin and an external object (e.g., a bed sheet). Shear also can occur when a high pressure area is adjacent to a low pressure area, thereby creating a pressure gradient that causes internal shearing effects.

Pressure sores generally result when shearing forces are exerted on an area of the body hat also is exposed to high pressure. Areas of the body that are particularly susceptible to pressure sores include tissues over the sacrum, ischial tuberosities, greater trochanters, external malleoli and heels. Other sites that are at risk for pressure sores often are based upon a particular patient's position and posture. Increased pressures under certain bony prominences depend upon postural position and changes affecting the tilt, obliquity and rotation of the pelvis when seated. In a lying position, more areas of an individual are prone to develop pressure sores because of the number of bony prominences that may be involved in weight bearing. Pressure of sufficient severity to impair local circulation in an immobilized patient causes local tissue anoxia (ischaemia) that progresses, if unrelieved, to necrosis of the skin and subcutaneous tissues within hours.

In an effort to distribute the external forces exerted on an individual, numerous types of cushions and mattresses have been developed. While no single pressure sore prophylactic device or procedure can prevent sores from ultimately developing, selective use of various procedures and devices minimizes the risk of pressure sore formation. To provide the best proper care for the patient, a clinician must possess knowledge of the complexities of pressure development, carefully observe the patient and compare the performance of different products and regimes.

To assist in this process, quantitative methods of pressure measurement are useful to evaluate and prescribe equipment designed to prevent or minimize pressure sore development. While pressure care regimes and equipment for postural control and pressure relief are abundant, pressure measurement devices and methods for understanding and quantifying the problem are still sparse. Those pressure measurement devices currently available to measure interface pressures employ a variety of different techniques to generate qualitative, semi-quantitative and quantitative results. Examples of such devices include those involving flexible sheets impregnated with acid indicators, electromechanical types using resistive, inductive or capacitive changes, strain gauges, pneumatics and electro-pneumatics. Some of these devices are sensitive to temperature and exhibit hysteresis owing to the nature of the materials used in their construction. These drawbacks limit their use in continuous or repetitive measurements because, for example, changes in temperature in the operating environment can introduce unacceptable drift in the output signal and adversely impact the sensitivity of the device. In practice, it has been difficult to design an ideal transducer for interface pressure measurement, and compromises between one or more of physical factors and safety, cost and ease with which a device can be used have become accepted in the industry.

Commercially available pressure measurement systems often employ a large array of sensors to provide mapping over the complete area of a support surface. The large number of sensors are monitored and evaluated by a computer system (e.g., a desktop or laptop computer system) which provides sufficient processing power to process the large amounts of data generated by the sensors. An example of such a system includes the "Xsensor" pressure mapping system sold by Roho, Inc. of Belleville, Ill. assignee of the present invention. These types of pressure measurement systems are not readily portable, and require considerable setup time and training for proper operation. Furthermore, a matrix (mat) of sensors is potentially the least accurate method of measuring pressure. A large mat of pressure sensors tends to introduce a large artefact into the pressure readings since the mat becomes a support surface in itself as a result of its hammock effect distributing the natural conformity of the support surface. Additionally, calibration of such as system is complex and requires considerable time.

Other pressure measurement techniques involve taping individual sensors directly onto the skin over a bony prominence where the highest pressures occur. Inaccuracies can arise in such an arrangement which influence the results if the sensors alter the pattern of stress so as to create a perturbation effect between the surfaces. Moreover, this procedure is time consuming, and requires advanced training and experience on the part of the clinician to properly position the sensors. As a result, single sensors are not practical for clinical practice.

Many therapists, nurses, doctors and patients cannot afford costly and complex systems such as the mat arrays which also are time consuming to use. However, they require information that helps identify problems, provides feedback about a particular surface and provides data as to whether the limits for tissue tolerance have been exceeded. This information is essential to properly compare support surfaces such as cushions and mattresses, and to fit and adjust seating systems and wheelchairs for a particular patient. Such pressure information also would be useful to inform and educate a caregiver or user about the best methods of pressure relief and their importance.

Therefore, it is desirable to develop a biomedical apparatus and method that improves chances of preventing pressure sores and discomfort, and overcomes the problems of the mat array pressure systems and the single sensor pressure systems. The apparatus preferably is an inexpensive, lightweight, portable device that is sized to fit in a person's hand or pocket. The biomedical apparatus should provide the clinician with a simple and quick indicator of a potential problem so that further investigation can be initiated, if required. It also should assist the clinician in monitoring the performance of support surfaces and comparing different products. The apparatus preferably is easy to use, self-calibrating, and does not require connection to a separate computer.

The biomedical apparatus preferably can be used as an assessment and prescription tool that provides a professional approach to pressure care situations. It should enable comparison and quantification of various support surfaces as part of the clinical assessment process, and facilitate the setup of pressure care equipment such as cushions, mattresses and stump sockets to ensure that optimum pressure relief is achieved. The device also should standardize procedures for assessment and prescription of pressure care devices to ensure continuity of assessment standards. The apparatus also should function as a research tool that allows for collection of historical data that can be compiled for retrospective analyses, as well as an educational and training tool for patients and students. The apparatus preferably provides biofeedback for the patient to reinforce strategies for weight shifts or reductions, and encourages compliance with the correct equipment. This biomedical apparatus also must be cost effective, and help to assist in the assessment of the most appropriate support device is prescribed for the patient. The device also can provide quantitative data for justifying and supporting applications to funding sources.

The hand-held unit preferably includes a removable sensor module that allows for one or more biomedical or physical sensors of various types to be connected to electronic circuitry disposed in the unit via one or more transducers. This configuration allows for the biomedical apparatus to be easily adapted to measure any of a wide range physical properties associated with a biologic or biomedical system, such as, for example, pressure, temperature, partial pressure oxygen ($PO_2$), carbon dioxide ($CO_2$), humidity, friction, force (weight and mass), displacement (linear & angular), radiant energy (optical) or blood flow.

BRIEF SUMMARY OF THE INVENTION

Accordingly, one object of the present invention is to provide an improved method and apparatus for measuring physical properties associated with a biomedical system to monitor and evaluate changes in physical properties associated with the biomedical system.

Another object of this invention is to provide an improved method and apparatus for measuring pressure at any interface between an individual's body and a surface to determine and evaluate physical stresses exerted on the body.

Another object of the present invention is to provide an improved method and apparatus that allows for evaluation of interface pressure over short periods of time to formulate trend analysis for long term use of a particular support device.

Another object of this invention is to provide an improved biomedical apparatus that is an assessment and prescription tool which enables comparison and quantification of various support surfaces as part of a clinical assessment process.

Another object of this invention is to provide a pressure measurement device that can be used as a therapeutic tool to assist in preventing the formation of pressure sores.

Another object of this invention is to provide a pressure measurement device that also can be used as a research tool to compile historical data that can be used for retrospective analysis and calculations (e.g., to calculate average, maximum, ratios or differences among pressures), and provide quantitative data for justifying and supporting applications to funding sources.

Another object of this invention is to provide a pressure measurement device that easily can be used by a patient or caregiver to provide biofeedback that reinforces pressure management strategies for weight shifts or reductions, and encourages compliance with requirements to correctly use support equipment.

Still another object of this invention is to provide an improved biomedical apparatus that is a small, inexpensive, lightweight, portable, hand-held, simple to operate, and provides quick and accurate measurements of interface pressure.

Another object of this invention is to provide an improved pressure measurement device that is self-calibrating.

Yet another object of this invention is to provide an improved biomedical apparatus that is battery powered.

Another object of this invention is to provide an improved pressure measurement device that facilitates setup of pressure care equipment such as cushions, mattresses and stump sockets to ensure optimum pressure relief is achieved, e.g., through footrest adjustment, varying inflation pressures, or bandaging.

Still another object of this invention is to provide an improved pressure measurement method and device that standardizes procedures for assessments and prescription of pressure care devices, and ensures continuity of assessment standards.

Another object of the present invention is to provide an improved method and apparatus for measuring and evaluating a range of physical properties including pressure, temperature, partial pressure oxygen ($PO_2$), carbon dioxide ($CO_2$), humidity, friction, force (weight and mass), displacement (linear and angular), radiant energy (optical) or blood flow to determine and evaluate physical stresses exerted on a surfaces or changes in the physical properties being monitored.

These and other objects will become apparent to those skilled in the art in light of the following disclosure and accompanying drawings.

In accordance with the invention, generally stated, a biomedical apparatus is provided that includes at least one biomedical or physical sensor that measures physical variables associated with biologic or biomedical systems such as a biological specimen or an entire organism and a hand-held unit including electronic circuitry for monitoring and evaluating the physical variables measured by the sensor. The apparatus can be used to measure and evaluate physical variables such as, for example, pressure, temperature, partial pressure oxygen ($PO_2$), carbon dioxide ($CO_2$), humidity, friction, force (weight and mass), displacement (linear and angular), radiant energy (optical) or blood flow associated with biomedical systems.

The type of biomedical sensor employed is dependent upon the particular physical property or properties to be evaluated. The sensor detects and measures in a quantitative fashion a physiological property of the biological or biomedical system. For example, noninvasive sensors can be used that do not even contact the biological system being monitored to measure physical properties such as radiant heat or sound energy coming from an organism. Other noninvasive sensors can be placed on the body surface to monitor physical properties (e.g., skin surface thermometers, biopotential electrodes and strain gauges). Minimally invasive sensors that are placed in a natural body cavity (e.g., oral-rectal thermometers, intrauterine pressure transducers and stomach pH sensors) and invasive sensors that are surgically implanted (e.g., needle electrodes, blood pressure sensors and blood flow transducers) also can be used. The physical variables and quantities measured by the sensors are converted by transducers into representative analog electrical signals. The analog signals then are converted to digital signals that are processed and evaluated by microprocessor-controlled electronic circuitry. A display assembly is included on the hand-held unit for providing information based upon the physical properties exhibited by the biomedical system. Thus, the biomedical apparatus can be used to monitor and evaluate a wide range of physical properties such as those listed above by employing appropriate physical sensors and transducers to measure the desired physical properties.

In the preferred embodiment, the transducers, a memory storage device and associated circuitry are mounted on a daughter board that is included in a removable sensor module associated with the hand-held unit. The memory storage device stores information representative of characteristics associated with the sensors and the transducers. The handheld unit also includes a main module to which the sensor module is removably secured. The components of the daughter board are electrically connected via a pin connector assembly to the microprocessor-controlled electronic circuitry which is mounted on a motherboard disposed in the main module. This configuration allows the sensor module to be easily and conveniently removed from the main module to replace the sensors and/or transducers if the apparatus is not operating properly, or to attach different types of sensors to the main module depending upon the particular physical properties to be evaluated.

Still another aspect of the present inventions is of a biomedical apparatus for monitoring and evaluating pressure at any interface between two abutting surfaces. The apparatus includes a sensor pad with at least one pressure sensor that is adapted to be disposed between the two surfaces to measure pressures exerted on one surface by the other surface, and generate data representative of measured pressures. At least one transducer further is included, with one transducer being in communication with each sensor for generating output signals representative of pressures measured by the sensor. Electronic circuitry is electrically connected to the transducers. The circuitry includes data processing circuitry electrically connected to the transducers for processing output signals generated by the transducer and generating pressure data based upon pressures measured by the sensor. A display is electrically connected to the data processing circuitry for visually displaying information representative of pressure data generated by the data processing circuitry. The circuitry is disposed in a hand-held housing, and the display is mounted on the housing. Tubing extends between the sensor pad and the housing for connecting each sensor to one transducer. A power source is disposed inside the housing for supplying power to the electronic circuitry.

In the preferred embodiment of the apparatus, the sensor pad includes the hydraulic pressure sensors and a hydraulic reference sensor. The fluid contained in the sensors is a hydrogenated synthetic hydrocarbon base fluid. Each sensor has a quadfoliate configuration resembling the shape of a four leaf clover. Tubing including a plurality of fluid filled tubes is employed that extends between the sensor pad and the housing to connect each sensor to one transducer. The reference sensor measures hydrostatic forces that may exist in the fluids contained inside the tubes. The transducer connected to the reference sensor generates output signals representative of hydrostatic forces measured by the reference sensor. The reference sensor output signals are processed by the data processing circuitry, and the data processing circuitry generates pressure data that is adjusted to compensate for the hydrostatic forces.

Yet another aspect of the present invention is of a portable biomedical apparatus for monitoring and evaluating pressures exerted on an individual by a surface against which at least a portion of the individual's body rests. The apparatus includes one or more sensor pads with at least three pressure sensors on each sensor pad. The sensor pad is adapted to be disposed between the individual's body and the surface to measure pressures exerted on the individual's body by the surface. The sensors generate data representative of measured pressures. At least three transducers are provided, with one transducer being in communication with each sensor for generating analog output signals representative of pressures measured by the sensor. Electronic circuitry also is provided that includes an analog to digital converter that is electrically connected to said transducers for converting the analog signals generated by the transducers to a digital signal representative of pressures measured by the sensors. A microprocessor is electrically connected to the analog to digital converter for performing a plurality of functions on the digital output signals generated by the analog to digital converter, and generating pressure data based upon pressures measured by the sensors. A display assembly is electrically connected to the microprocessor for displaying pressure information based upon output data generated by the microprocessor. In the preferred embodiment, the display assembly includes a LCD screen and an LED bar graph. A hand-held housing also is included in which the electronic circuitry is disposed, and on which the display is disposed.

Tubing extends between the sensor pad and the housing for connecting the sensors to the transducers. A power source (e.g., a battery) is disposed inside the housing for supplying power to the electronic circuitry.

Another aspect of the present invention is of a sensor pad for measuring pressures at an interface between two surfaces. The sensor pad includes at least one hydraulic sensor having a quadfoliate configuration. In one illustrative embodiment of the sensor pad, at least three hydraulic sensors are disposed in a matrix configuration to provide a surface area that covers a bony prominence of an individual. The sensor can be a fluid-filled cell having a hydrogenated synthetic hydrocarbon base fluid disposed in the cell.

Still yet another aspect of the present invention is that of a method for evaluating pressure exerted on a first surface by a second surface, including the steps of measuring pressures exerted on the first surface by the second surface at two or more different locations; comparing pressures measured at the different locations to determine a maximum measured pressure; comparing pressures measured at the different locations to determine an average measured pressure; and determining a pressure index based upon the difference between the maximum measured pressure and the average measured pressure. The method also can include the steps of determining a maximum pressure trend based upon maximum measured pressures over a predefined period of time, and determining an average pressure trend based upon average measured pressures over the predefined period of time.

Other objects and features will be apparent and in part pointed out hereinafter.

BRIEF DESCRIPTION OF THE SEVERAL VIEWS OF THE DRAWINGS

The objects of the invention are achieved as set forth in the illustrative embodiments shown in the drawings which form a part of the specification.

In the drawings.

FIGS. 8A–8G are schematic diagrams further illustrating and identifying various components shown in FIG. 8;

Corresponding reference characters indicate corresponding parts throughout the several views of the drawings.

DETAILED DESCRIPTION OF THE INVENTION

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention.

Figure 1:
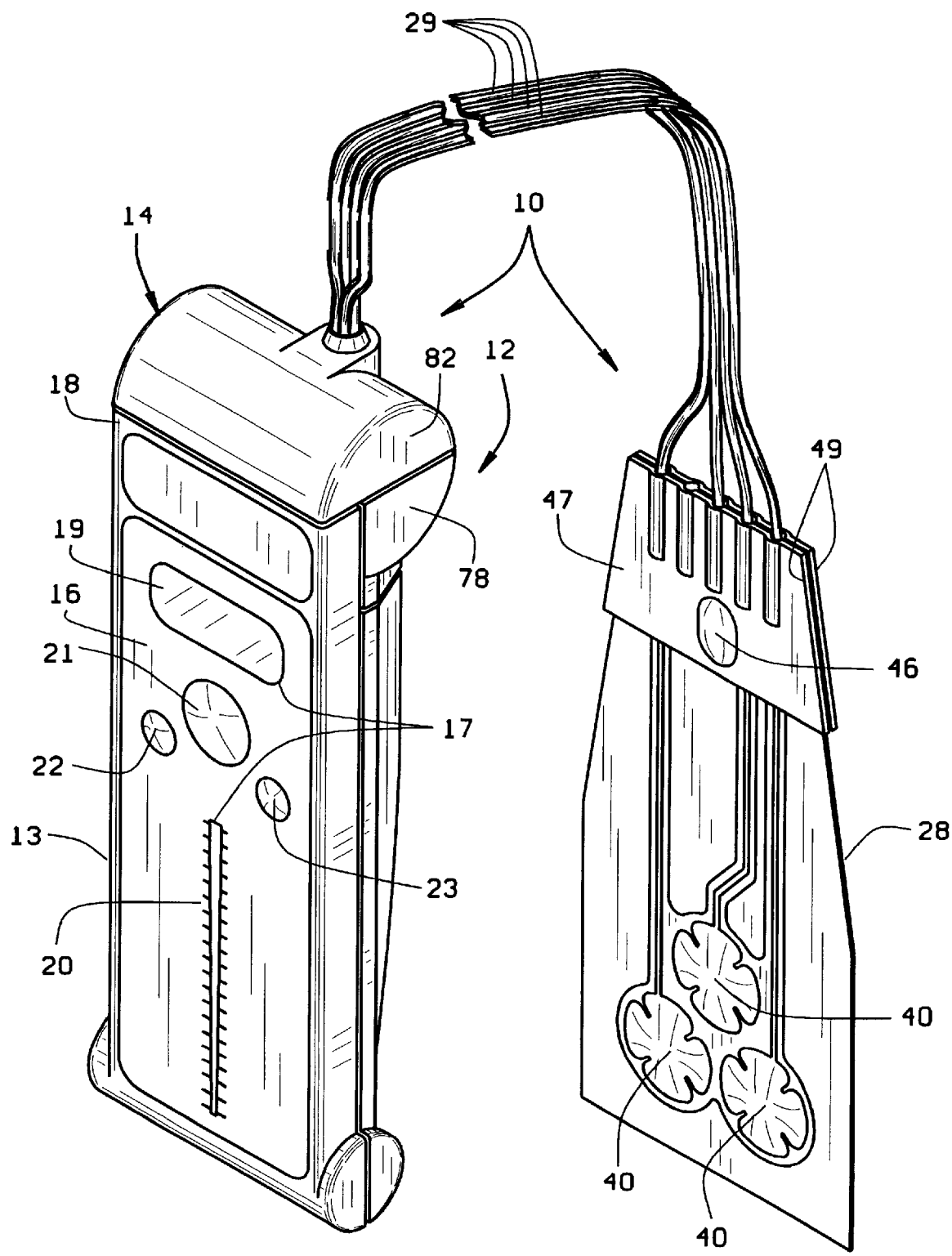
FIG. 1 is a perspective view of one illustrative embodiment of the biomedical apparatus of the present invention adapted for measuring pressure at an interface between two surfaces.

Referring now to the drawings, and in particular FIG. 1, an illustrative embodiment of a biomedical apparatus of the present invention is shown, referred to generally by reference number 10, that is adapted to measure and evaluate pressure at any interface between two surfaces. For example, the apparatus 10 can be used to measure pressure at any interface between an individual's body and a surface to determine and evaluate physical stresses exerted on the body. The biomedical apparatus 10 includes a hand-held unit 12, with a control panel 16 being on a front surface 18 of the hand-held unit 14. In the preferred embodiment, hand-held unit 14 has an overall length of approximately 8 inches and a width of approximately 3 inches. The control panel 16 preferably includes a display assembly 17 having a liquid crystal display (LCD) screen 19 and a light emitting diode (LED) bar graph display 20. The control panel 16 also includes three function push-button switches, namely, a mode button 21, a power button 22 and an increment button 23, that control execution of a multitude of operations performed by electronic circuitry 26. The electronic circuitry 26 (discussed below and shown in FIGS. 7 and 8) is housed inside the hand held unit 12, and connected to at least one sensor pad 28 via tubing 29. While the following discussion and drawings illustrate only one sensor pad 28 connected to the hand-held unit 12, it will be appreciated that additional sensor pads can be connected to the hand held unit 12 if desired for a particular application.

As discussed below and shown in FIGS. 9–11, the hand held unit 12 preferably includes a main module 13 and a sensor module 14 that is adapted to be removably secured to the main module 13. As further discussed below and shown in FIGS. 8, 8A and 11 components including transducers PS1–PS4, a memory storage device IC1 and associated circuitry are mounted on a daughter board 62 and disposed in the sensor module 14. The sensor pad 28 is connected to the transducers PS1–PS4 via tubes 29. The components mounted on the daughter board 62 are electrically connected to electronic circuitry 26 mounted on a motherboard 62 (see FIGS. 8 and 8B–8G) via a pin connector assembly P1 & P2. The motherboard 62 is disposed in the main module 13.

In the illustrative embodiment shown in the drawings, the sensor pad 28 is adapted to allow for pressure measurement at an interface between two surfaces. However, as discussed herein, the sensor pad 28 can easily be replaced with one or more types of biomedical or physical sensors to allow for measurement and evaluation of a wide range of physical properties. For example, noninvasive, noncontact sensors can be used to measure physical properties such as radiant heat or sound energy coming from an organism. Other noninvasive sensors can be placed on the body surface to monitor physical properties (e.g., skin surface thermometers, biopotential electrodes and strain gauges). Minimally invasive sensors that are placed in a natural body cavity (e.g., oral-rectal thermometers, intrauterine pressure transducers and stomach pH sensors) and invasive sensors that are surgically implanted (e.g., needle electrodes, blood pressure sensors and blood flow transducers) also can be used to measure physical variables. Regardless of the type of sensor used, each sensor is in communication with a transducer that generates an electrical signal based upon the measured physical variables and quantities.

For pressure measurement applications, the sensor pad 28 associated with the preferred embodiment includes a plurality of sensors 40 that are disposed in a matrix configuration to provide sufficient surface area to cover a bony prominence of an individual, to fit inside a limb socket and to fit under a bandage. The sensors 40 preferably are hydraulic sensor, with each sensor being a fluid filled cell. In the preferred embodiment, the sensor pad 28 includes three hydraulic sensors 40 that provide sufficient area to cover a bony prominence of an individual. However, it will be appreciated that the number, arrangement and design of the cells 40 can be varied, if desired, to provide additional data points. For example, if the dimensions of the sensor pad are increased so that the sensor pad is a full mattress pad, the number of sensors also increases to allow for pressure measurements at interfaces between the patient and the pad when lying on the mattress. The tubing 29 connecting the sensors 40 to the circuitry 26 includes fluid-filled tube connectors, with each sensor 40 being in fluid communication with the electronic circuitry 26 via pressure transducers PS1–PS4 (discussed below and shown in FIGS. 7, 8 and 11). The fluid contained in the sensor cells 40 preferably is totally inert and does not interact with the plastic tube connectors 29 in which it is disposed.

The hydraulic sensors 40 offer several advantages over other types of pressure sensors, such advantages including continuous, stable and repeatable readings that are linear with a high frequency response (i.e., greater than 30 Hz minimum). All of these factors are particularly important in a dynamic environment. The fluid of the sensors 40 preferably has a specific gravity slightly less than water, and maintains desirable properties and viscosity when exposed to a broad range of temperatures to which the apparatus 10 may be exposed (e.g., from 0° C. to 140° C.). In the preferred embodiment, the fluid is DURASYN® 162 Polyalphaolefin, sold by Amoco Chemical Company, Lisle, Ill., that is a hydrogenated synthetic hydrocarbon base fluid typically used in fully and partially synthetic, premium, long-drain lubricating oils, industrial oils, hydraulic fluids, transmission fluids and heat transfer fluids. This fluid has been approved by the United States Federal Drug Administration (FDA), and exhibits desirable features including thermal stability, oxidation resistance and low-temperature fluidity. It has a specific gravity of 0.8 at 15.6° C., and a viscosity of 1.6–2.1 CST. at 100° C. (212° F.).

Figure 2A:
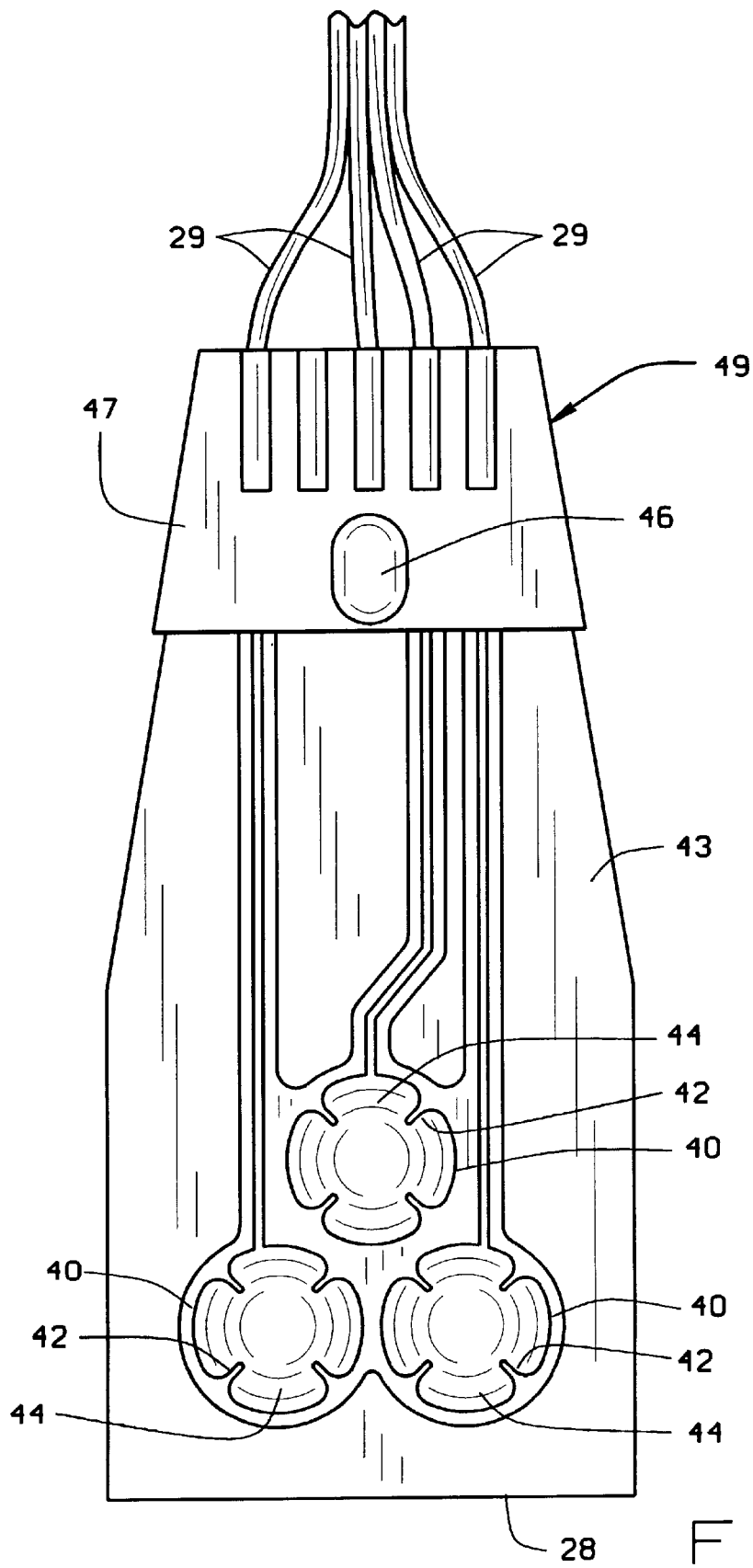
FIG. 2A is a front elevational view of the sensor pad.

The hydraulic sensors 40 also have a unique cell geometry and design as shown in FIG. 2A. More specifically, each cell 40 has a quadfoliate configuration resembling that of a four leaf clover. In other words, each cell 40 has a substantially circular shape with four notches 42 extending radially inwardly from the circumference of the circle so as to define four "leaves" 44 of the clover shape. This unique shape prevents the cells 40 from ballooning as the diameter of each cell increases, and thus reduces the perturbation effects at the interface. By preventing ballooning or bulging of the fluid filled cells during operation of the apparatus 10, pressure readings generated by the sensors have a higher degree of accuracy than would otherwise result in the absence of this unique cell design. It will be appreciated that the number of leaves can be increased or decreased by varying the number of notches.

The cell configuration shown in FIG. 2A occupies sufficient surface area to adequately cover an area being measured. The sensor pad 28 preferably is positioned directly against the skin at any location on the body. Alternatively, the clinician can place the sensors 40 on a support surface rather than placing them directly onto the skin.

Human tissue is favorably compliant under low strains so that the load is distributed evenly over the sensors 40. The four leaf clover shape is preferred for the cells 40 because it allows for minimal perturbation so as to restrict deformation and disturbance of the surfaces for which pressure measurements are sought. The thickness of the cell 40 is an aspect ratio, and is a function of diameter. For a cell of approximately 20 mm in diameter, the cell thickness preferably is less than or equal to 2 mm to obtain minimal perturbation effect and provide a high degree of accuracy in the pressure readings.

The sensor pad 28 is sized so as to not introduce hammock effects that can occur when large mat array systems are employed. In the preferred embodiment, the overall dimensions of the sensor pad 28 are approximately 90 mm in width at the end of the pad 28 in which the sensors 40 are disposed, tapering to approximately 55 mm in width at the end from which the tubing 29 extend, approximately 186 mm in length, and less than 1 mm in thickness. Three pressure sensors 40 are used in the preferred embodiment shown in FIGS. 1 and 2 to provide a minimum number of data points to interrogate and generate meaningful trend analysis. The sensor 40 configuration of FIG. 2 also is preferred because it allows for the pressure measurement device to be manufactured at a minimal cost. Increasing the number of cells 40 beyond three would increase the complexity and cost of the device.

Figure 2B:
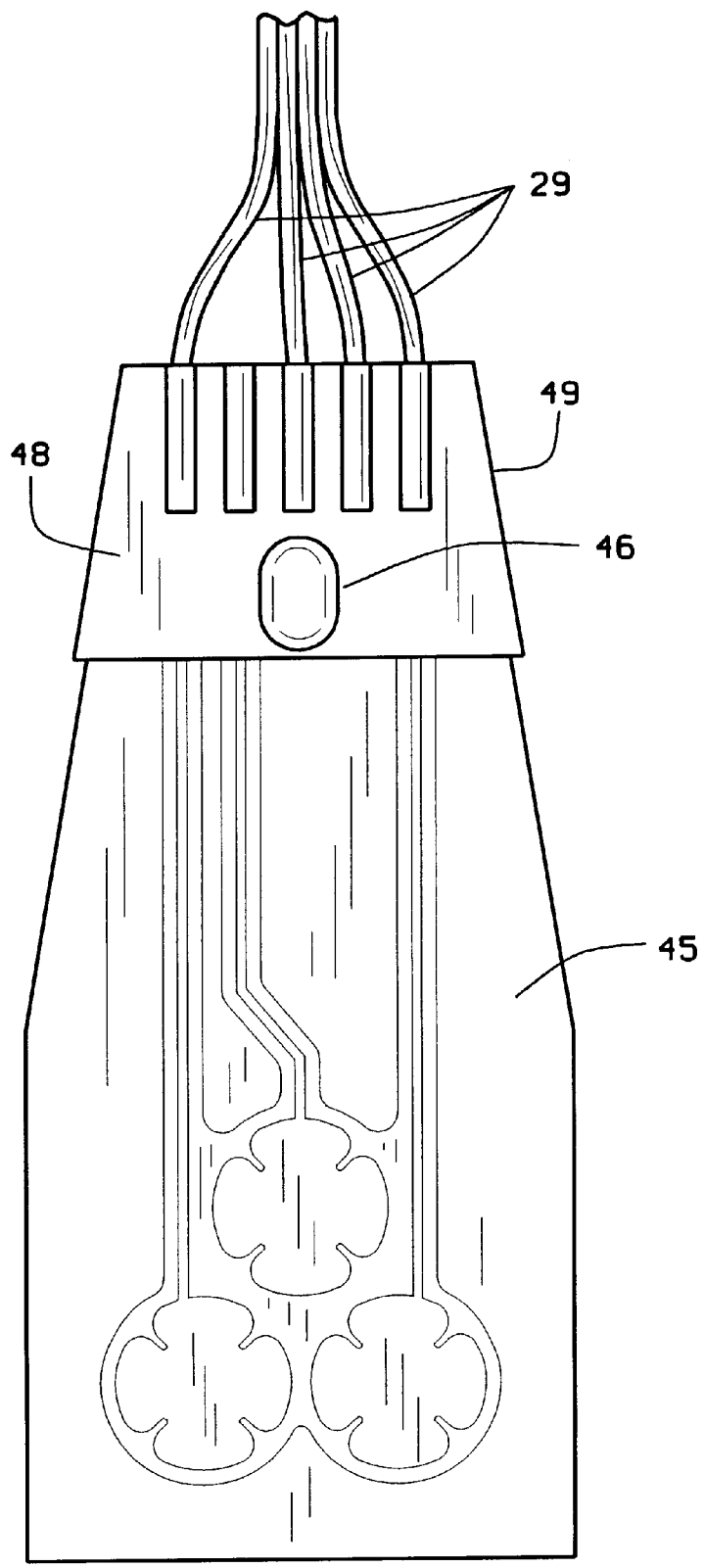
FIG. 2B is a back elevational view of the sensor pad shown in FIG. 2A.

The cells 40 preferably extend outwardly from only one side of the sensor pad 28 as shown in FIGS. 2A and 2B. However, cells 40 can be disposed on both sides of the sensor pad 28, if desired. FIG. 2A shows a front elevational view of a front surface 43 of the sensor pad 28 having the sensors 40 extending outwardly therefrom, and FIG. 2B shows a back elevational view of a back surface 45 of the sensor pad 28 that is opposite to front surface 43 (e.g., a bottom surface). It will be appreciated that the front surface preferably is positioned against the patient or object exposed to pressure during operation of the apparatus 10.

The sensor pad 28 of the preferred embodiment also includes a hydraulic reference sensor 46 that is used to compensate for hydrostatic forces that may exist in the column of fluids inside the tubing 29 that connect the hydraulic sensors 40 to the transducers PS1–PS4 (discussed below). The reference sensor 46 preferably is disposed between front and back plates 47, 48, respectively, of a hard plastic clamp 49 that connects tubing 29 to the sensors 40 46. This configuration is preferred because it protects the reference sensor 46 from external pressure exerted on the sensor pad 28. In this arrangement, the reference sensor 46 acts as a manometer measuring hydrostatic forces. An artefact could be introduced into the pressure measurement readings in the absence of such a reference sensor. When the pressure sensors 40 are moved vertically above or below the height of the hand-held unit 12, the measured pressures have an error which is introduced by effects of hydrostatic forces. In other words, in the absence of such a reference sensor, if the sensors 40 were elevated above the hand-held unit 12, the pressure readings would be artificially high and, conversely, the pressure readings would be artificially low if the sensors 40 were placed below the level of the hand-held unit 12. The magnitude of the error that would be introduced (without compensation) is approximately ±0.7 mmHg pressure per 10 mm change in height of the sensor pad 28 with respect to the hand-held unit 12. This artefact is removed by an auto-zeroing function performed by the microprocessor IC4 associated with the circuitry 26 that continuously compensates for hydrostatic forces based upon the pressure detected by the reference sensor 46. The reference sensor 46 continuously monitors the level of hydrostatic pressure so that the microprocessor IC4 can compensate for this pressure when generating the pressure readings by subtracting the effects of hydrostatic pressure from the pressures measured by the reference sensors 40.

Figure 5:
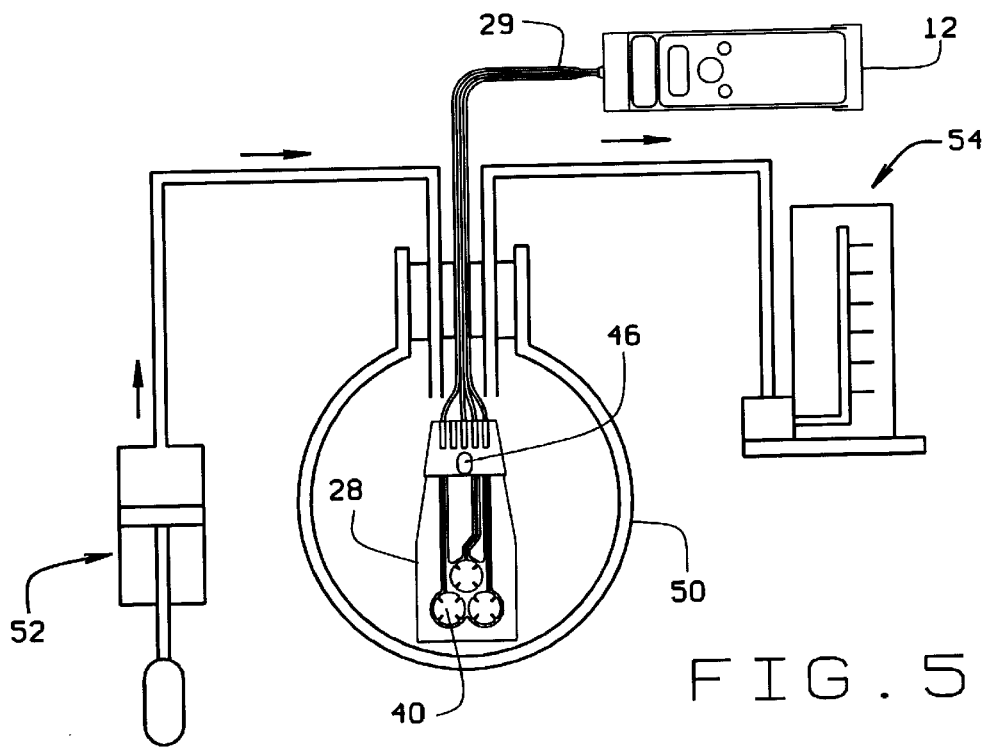
FIG. 5 is a schematic diagram illustrating ideal testing conditions in which the sensor pad is disposed inside an air chamber that is connected to a pressure pump system and a mercury manometer for measuring actual applied pressures.
Figure 6:
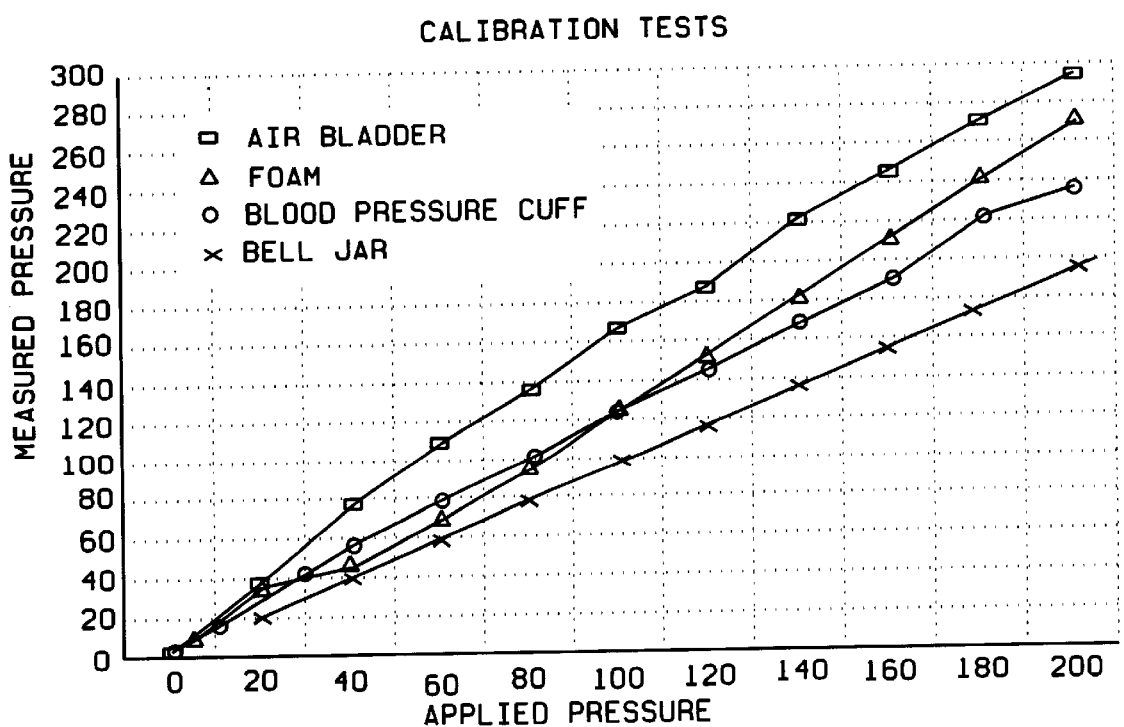
FIG. 6 is a chart comparing applied pressures to pressures measured by the apparatus when the sensor pad is positioned between a variety of surfaces.

The pressure measurement device 10 provides a realistic value for the pressure measured by the sensors 40 at the interface in a wide variety of conditions ranging from ideal to relatively hostile conditions that can occur at the interface between the body and a support surface. In ideal conditions when the sensors 40 are placed in an air chamber 50 connected between a pressure pump system 52 and a mercury manometer 54 and are not deformed (see FIG. 5), the apparatus 10 generates pressure results that are within 1 mmHg of the actual applied pressure over a range of 0 to 200 mmHg. The pressure readings also are highly stable, producing a linear output that is not sensitive to temperature and exhibits negligible hysteresis (less than 1%). The apparatus 10 exhibits exceptional long term stability which is achieved by incorporating a digital electronic system coupled to hydraulic sensors. The apparatus 10 exhibits drift of less than five percent (5%) over extended periods of time in varying conditions, and superior repeatability of measurements. FIG. 6 illustrates test results when the sensor pad 28 is placed between less compliant surfaces including a bell jar, foam, a bladder and a blood pressure cuff. In these situations, the results are generally linear, but exhibit an increasing error as the pressure applied to the sensor pad 28 is increased. Less deviation occurs when the sensor pad 28 is positioned against the soft tissues of the forearm and the lower leg with a blood pressure cuff applying pressure. These results demonstrate that superior pressure measurements are obtained at the interface because the favorable compliance of human tissue under low strains ensures that the load is distributed evenly over the sensors' surface. Other test materials, such as foam and the bladder, have surface tensions that are significantly higher than that of human tissue, and thus, their compliance is not as favorable as human tissue with respect to their ability to envelop the sensors 40 (see FIG. 6). In other words, accuracy approaches the ideal as compliance of the interface increases.

To compensate for errors or perturbing effects produced by noncompliance at the body interface, the apparatus 10 has a correction factor programmed in the memory device IC1 associated with the daughter board 62 mounted in the sensor module 14 that offsets such errors. The correction factor provides a further improvement in the accuracy of the readings shown in FIG. 6.

As discussed above, the biomedical apparatus 10 can be adapted to monitor and evaluate a wide range of physical properties associated with biologic or biomedical systems, including, but not limited to, pressure, temperature, partial pressure oxygen ($PO_2$), carbon dioxide ($CO_2$), humidity, friction, force (weight and mass), displacement (linear and angular), radiant energy (optical) or blood flow associated with biomedical systems, by simply changing the type of sensors and transducers employed for a particular application. The type of biomedical sensor employed is dependent upon the particular physical property or properties to be evaluated. The sensor detects and measures in a quantitative fashion a physiological property of the biological system. As discussed above, examples of physical sensors that can be connected to the hand-held unit 12 include noninvasive noncontact sensors, noninvasive contact sensors, minimally invasive sensors and invasive sensors.

The sensor pad 28, tubing 29 and sensor module 14 (including the transducers PS1–PS4 and daughter board 62) can be easily removed from the mother board 60 associated with the main module 13 of the hand-held 12. Providing the ability to easily remove the sensor module 14 and sensor pad 28 from the main module 13 and motherboard 60 allows the main module 13 and motherboard 60 to be used in conjunction with a wide range of sensors and transducers in a variety of different applications. The main module 13 and motherboard 60 can be connected to appropriate sensors and transducers via pin connectors P1 and P2 to measure and evaluate a wide range of physical variables and quantities for a particular biologic or biomedical system. Each sensor is in communication with a transducer that generates analog electrical signals representative of the measured physical variables. The analog signals then are converted to digital signals that are processed and evaluated by microprocessor-controlled electronic circuitry 26 (see FIGS. 7 and 8, and discussion below). The display assembly on the hand-held unit 12 provides information based upon the physical properties exhibited by the biomedical system. Thus, the biomedical apparatus can be used to monitor and evaluate a wide range of physical properties such as, for example, pressure, temperature, partial pressure oxygen ($PO_2$), carbon dioxide ($CO_2$), humidity, friction, force (weight and mass), displacement (linear and angular), radiant energy (optical) or blood flow, by employing appropriate physical sensors and transducers to measure the desired physical properties.

Information representative of pressure exerted on the sensors 40, 46 is transmitted from the sensors 40, 46 to the circuitry 26 via the transducers PS1–PS4. The circuitry 26 includes a microprocessor IC4 (see FIGS. 7 and 8) that performs input, processing, storage, output and control functions to accomplish operations on data based upon signals generated by the transducers PS1–PS4 (discussed below). In the preferred embodiment, the particular functions performed by the circuitry 26 are based upon the settings of the three function button switches 21, 22, 23 associated with the control panel 16 and electrically connected to the circuitry 26 (i.e., the power button 22, the mode button 21, and the increment button 23). The power button 22 controls actuation of the circuitry 26 by toggling the apparatus 10 off and on when the button 22 is pressed. The power button 22 also is used to initiate a self-calibration mode, discussed below.

The mode button 21 is pressed to cycle the microprocessor IC4 through a plurality of modes of operation. Alphanumeric symbols representative of each mode of operation are sequentially displayed on the LCD screen 19 when the button 21 is pressed to indicate which mode currently is selected. In the preferred embodiment, the following symbols and modes are employed: "P" for maximum pressure mode; "A" for average pressure mode; "rAP" for maximum pressure trend mode; "rAA" for average pressure trend mode; "PI" for pressure index mode; "t" for threshold adjustment mode; "SrA" for set trend period (seconds) mode; and "U" for set units of measurement (mmHg or kPa) mode. It will be appreciated that the microprocessor IC4 can be programmed to perform other analyses and calculations in addition to or instead of those associated with the foregoing modes of operation, depending upon the physical properties being evaluated and particular applications for which the apparatus 10 is used.

In the preferred embodiment, the mode button 21 is pressed to sequentially cycle through the modes of operation. The increment button 23 is used to perform the following functions: (1) when the apparatus 10 is in the maximum pressure mode "P" or the average pressure mode "A" as indicated on the LCD screen 19, the increment button 23 can be pressed to toggle between the maximum pressure mode "P" and average pressure mode "A"; (2) when the apparatus is in the maximum pressure trend mode "rAP" or the average pressure trend mode "rAA", the increment button 23 can be pressed to toggle between these two modes; (3) when the apparatus is in the threshold mode "t", the increment button 23 can be pressed to adjust a threshold pressure level to a desired pressure level; (4) when the apparatus is in the set trend period mode "SrA", the increment button 23 can be pressed to adjust the period of time over which pressure trends (rolling average) are calculated; and (5) when the apparatus is in the set units of measurement mode "U", the increment button 23 can be pressed to toggle between the symbols of "Hg" and "Pa" displayed on the screen 19 to select the desired units of mmHg or kPa, respectively, of pressure measurement.

The electronic circuitry 26 associated with the pressure measurement device 10 controls the operation of the device 10 based upon input signals received from the buttons 21, 22, 23 and the sensors 40, 46. To actuate the pressure measurement device 10, the power button 22 is pressed one time to turn on the device. If the power button 22 is pressed again, the device 10 is turned off. If the device 10 is on and remains idle for five minutes, the circuitry 26 automatically turns off to conserve battery power.

As discussed above, the apparatus 10 includes a self-calibration function that is performed by the microprocessor IC4 to ensure a high degree of accuracy in the pressure readings. To activate the self-calibration routine, the power button 22 is pressed at start-up for a set time interval (e.g., approximately five seconds), and a symbol "Cal" appears momentarily on the screen 19, indicating that the circuitry 26 is performing its calibration routine. While the calibration routine is performed, it is important to ensure that the sensor pad 28 is free from any external pressure, and resting on a horizontal surface, preferably the surface against which pressure is to be measured. The sensor pad 28 should not be held by a person, or placed under any object during execution of the calibration routine. During the calibration routine, the microprocessor determines a zero pressure value for which no interface pressure detected by the sensors. The zero pressure value represents a reference point at which zero input from the sensors coincides with zero output for the transducers. When the microprocessors IC4 executes the self calibration routine, the microprocessor IC4 resets the zero point and full-scale deflection of 272 mmHg on a linear calibration curve. This zero pressure value is used by the microprocessor as a reference point in subsequent pressure computations performed by the microprocessor during operation of the device 10. Linearity of the circuitry 26 and the transducers PS1–PS4 allows the self-calibration routine to be easily and accurately performed by the microprocessor. When the calibration routine is completed, the microprocessor IC4 defaults into the maximum pressure mode, indicating that the sensors 40, 46 are properly calibrated.

When the device 10 is turned on, the screen 19 and bar graph 20 default to display the maximum pressure mode "P". Maximum pressure refers to the highest pressure measured by any of the three pressure sensors 40 on the pad 28. In this mode, the microprocessor IC4 compares the measured pressures, and determines the maximum pressure measured by any of the pressure sensors 40. The circuitry 26 samples pressures measured by the sensors 40 three times per second, and displays the highest pressure value that is measured by the sensors 40 in the maximum pressure mode. This method of maximum pressure measurement reduces the need for exact placement of the sensor pad 28 over a bony prominence and allows for bodily movements during operation of the device 10.

After the device 10 is turned on and the symbol for the maximum pressure mode "P" is displayed on the screen 19, the device 10 can be used to measure the desired pressures at an interface between two surfaces by placing the sensor pad 28 at a desired location. The mode of operation can be changed from the maximum pressure mode by pressing the mode button 21. Pressing the mode button 21 once causes the microprocessor IC4 to switch into the average pressure mode and the screen 19 to display the symbol "A". The screen 19 and bar graph 20 then simultaneously display the average pressure measured across all three pressure sensors 40. In this mode, the microprocessor IC4 determines the average pressure based upon pressures measured by the sensors 40. As discussed above, the increment button 23 also can be pressed when the microprocessor IC4 is in the maximum pressure mode P or the average pressure mode A to switch between these two modes.

As discussed above, the mode button 21 can be pressed repeatedly to cycle through the various modes of operation associated with the apparatus 10. The screen 19 displays the appropriate symbol as set forth above for each mode. The clinician stops pressing the mode button 21 when the symbol associated with the desired mode of operation is displayed on the screen 19. The pressure trend calculated by the microprocessor IC4 and displayed on the screen 19 and bar graph 20 in the average pressure trend mode rAA represents a rolling average pressure of pressures measured by the sensors 40 over time. Similarly, the pressure trend calculated and displayed in the maximum pressure trend mode rAP represents a rolling average of maximum pressures measured by the sensors 40 over time. The time interval over which the pressure trends rAA and rAP are evaluated is referred to as the "trend period", and is set by the clinician or operator in the set trend period mode SrA, as discussed below. As discussed above, the increment button 23 can be pressed when the apparatus 10 is in the maximum pressure trend mode rAP or the average pressure trend mode rAA to switch between these two modes.

To illustrate calculations executed by the microprocessor IC4 to determine the maximum pressure trend and average pressure trend, consider the following example in which a series of ten pressure values are generated by the sensors 40. These pressure values (mmHg) are 30, 45, 67, 78, 23, 43, 89, 102, 21 and 99. To determine the average pressure, the ten numbers are added together and divided by 10. The average pressure of these values is 60 mmHg, rounded to the nearest whole number. Assuming the next pressure value received by the circuitry is 134, this value is added to the existing ten values, and the first value in the resulting sequence is deleted to give the new series of 45, 67, 78, 23, 43, 89, 102, 21, 99 and 134. The new average pressure based upon this series is 70 mmHg, rounded to the nearest whole number. Thus, the average pressure trend is continuously updated by the microprocessor IC4 for a set of pressure values, and provides time related results, smoothing out variations in pressure considered to be insignificant by rounding to the nearest whole number.

In the pressure index mode "PI", the microprocessor IC4 calculates and displays on the LCD screen 19 a pressure index based upon the difference between the maximum pressure and the average pressure. In other words, pressure index=(maximum pressure)−(average pressure). When the pressure index is zero, pressure is evenly distributed over the surface area being evaluated. For example, when a patient rests against a less compliant surface such as a foam support, a higher pressure index is obtained than when the patient rests against a more compliant surfaces such as an air cell cushion manufactured by Roho, Inc. of Belleville, Ill. Thus, as the pressure index decreases, the fit between the support surface and the patient becomes more desirable. The pressure index is a unique calculation and measurement that is not performed by conventional pressure measurement systems. The pressure index provides useful information when evaluating pressure at an interface, and is weight independent. Furthermore, pressure index calculations are independent of the accuracy of the instrument because any error is effectively removed from the equation.

To set the trend period during which the set of pressure values are accumulated for the maximum pressure trend analysis and the average pressure trend analysis, the mode button 21 is pressed until the screen 19 displays "SrA" for the set trend period mode. The increment button 23 then is pressed until the desired time interval is displayed on the screen 19. In the preferred embodiment, the trend period can be adjusted in one second intervals in the range of 1 to 60 seconds. When the desired time period is displayed, the clinician stops pressing the increment button 23 to select the displayed time interval. The selected trend period applies to both the maximum and average pressure trend analyses rAP and rAA.

Figure 3:
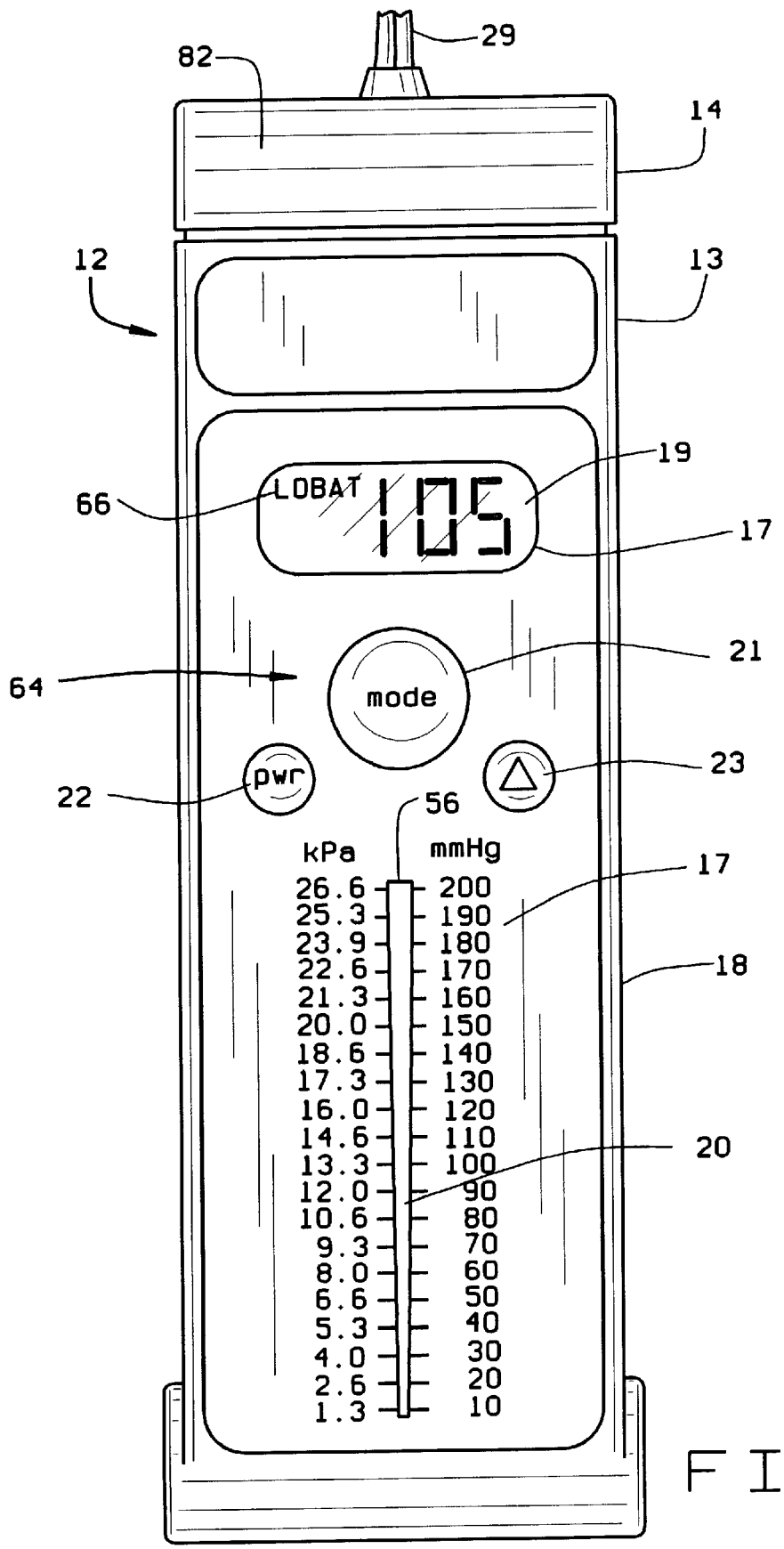
FIG. 3 is a front elevational view of hand held unit showing the LCD screen, LED bar graph and 3 function buttons.
Figure 7:
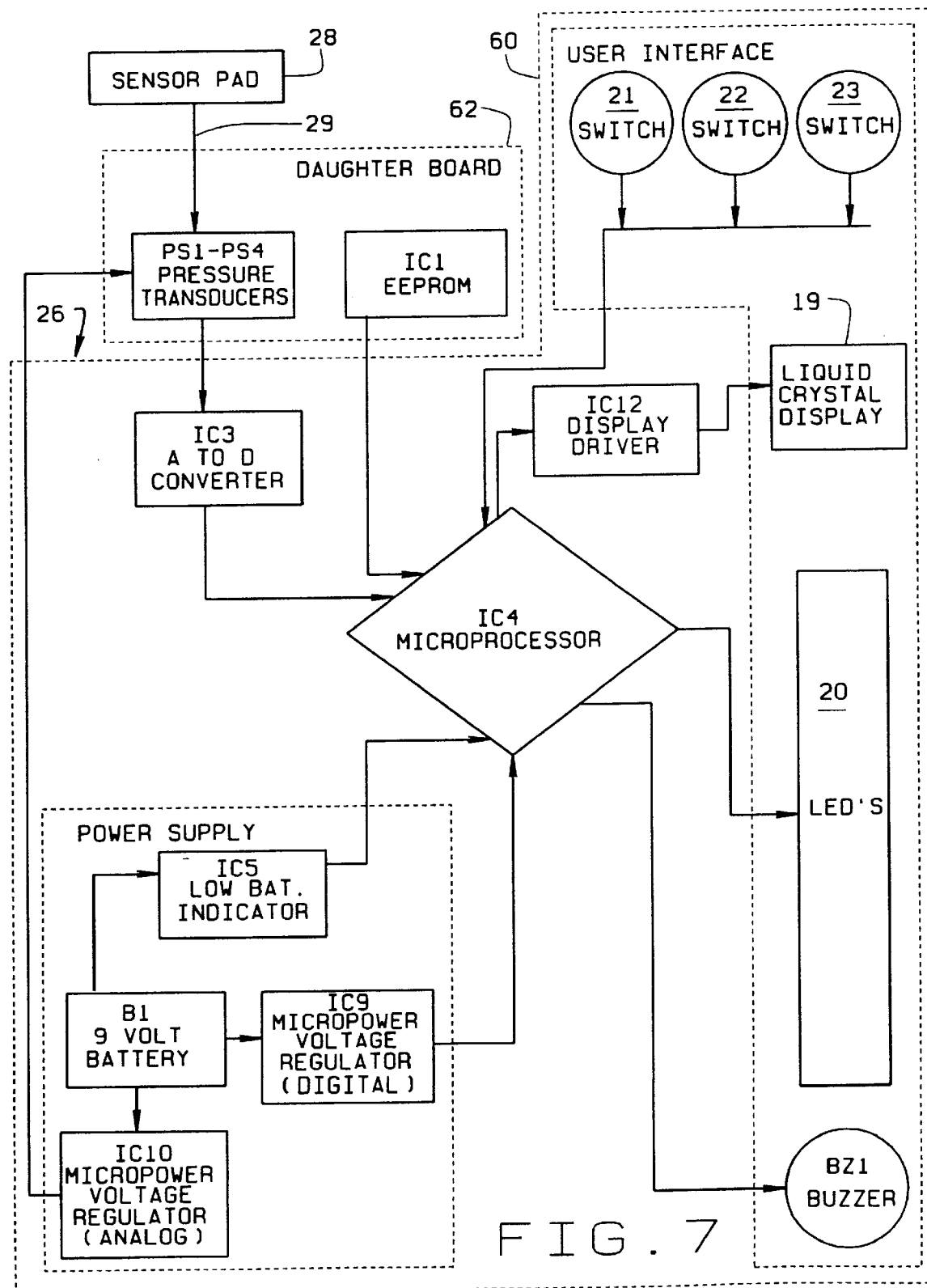
FIG. 7 is a block diagram schematically illustrating electronic circuitry associated with the biomedical apparatus of FIG. 1.
Figure 8:
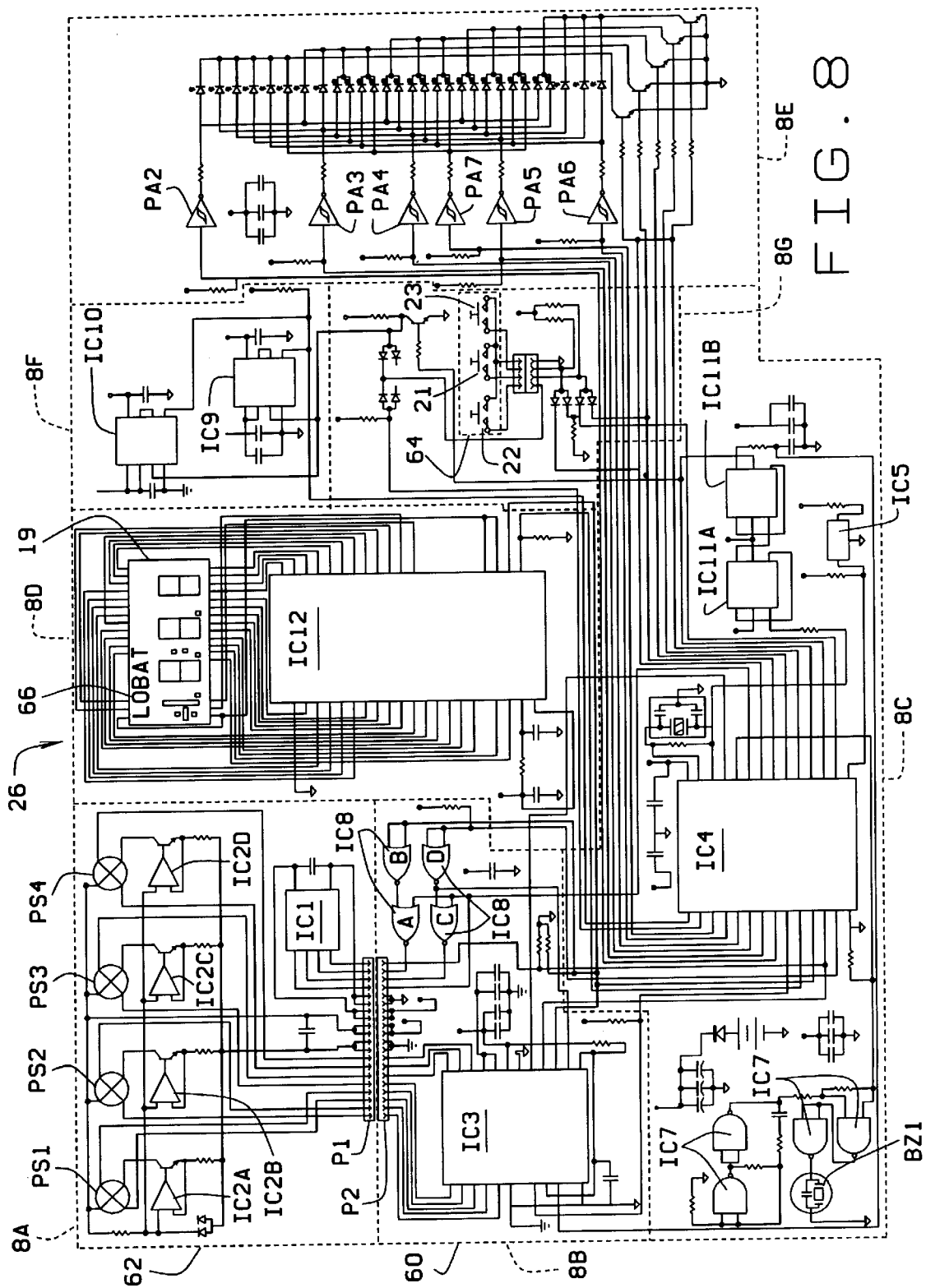
FIG. 8 is a schematic diagram illustrating one embodiment of the electronic circuitry associated with the biomedical apparatus shown in FIG. 7.

To set the desired threshold value, the mode button 21 is pressed until the symbol "t" is displayed on the screen 19. As discussed below, measured pressure levels can be compared to the threshold level on the bar graph display 20. After the symbol "t" is displayed, the screen 19 then displays a predefined'threshold value, preferably within a preprogrammed range of 30 to 120 mmHg (i.e., the normal range of blood pressure). The increment button 23 can be pressed to change the predefined threshold value to a desired value within the preprogrammed range, with the displayed value being increased in 10 mmHg increments. A plurality of light emitting diodes (LEDs) LD1, LD2, LD3, LD4, LD5, LD6, LD7, LD8, LD9, LD10, LD11, LD12, LD13, LD14, LD15, LD16, LD17, LD18, LD19 and LD20 are included in the bar graph 20, as shown in FIGS. 3 and 7, with at least one LED being disposed at a location corresponding to each value of mmHg or kPa that is labeled on the control panel 16. The LEDs extend in a row outwardly through an opening 56 formed in the housing so as to be visible by the operator of the biomedical apparatus 10. As discussed below, LEDs LD1–LD8 preferably emit a first color or hue (e.g., red), and LEDs LD18–LD20 preferably emit a second color or hue (e.g., green). LEDs LD9–LD17 preferably are bi-color LEDs that emit both the first and second colors or hues (e.g., red and green). When the threshold value is adjusted in the preferred embodiment, the LEDs associated with pressure values greater than the threshold value are illuminated in one color (e.g., red), and LEDs associated with pressure values less than or equal to the threshold value are illuminated in a different color (e.g., green). The threshold value can be used to represent a level of tissue tolerance that is set by the clinician. The threshold value also can be used as a comparative level of pressure. In this situation, the threshold value can be set to the average pressure obtained from a first surface, and then an average pressure of a second surface can be compared and evaluated in view of the average pressure value from the first surface.

The components mounted on the daughter board 62 of the sensor module 14 and the electronic circuitry 26 disposed in main module 13 of the hand-held unit 12 are illustrated in FIGS. 7, 8 and 8A–8G. This circuitry 26 controls the operation of the apparatus 10, and executes the various modes of operation based upon inputs from the sensors 40, 46 and settings selected by the clinician via the function buttons 21, 22, 23. As shown in FIGS. 7, 8, 9 and 11, the daughter board 62 is plugged into the motherboard 60 via a pin connector assembly including connectors P1 and P2. As discussed above and below, the sensor module 14 is adapted to be removably secured to the main module 13. A plug-in three switch membrane 64 (FIG. 3) is bonded onto the front surface 18 of the main module 13 on the control panel 16. The three push-button switches 21, 22, 23 are disposed below corresponding labels on the membranes, so that the mode switch 21 is actuated when a "MODE" label is pressed, the power switch 22 is actuated when a button "PWR" button label is pressed, and the increment switch 23 is actuated when a "Δ" button label is pressed. Outputs generated by the circuitry 26 are displayed or communicated to the clinician on the LCD screen 19, on the bar graph 20, and by a one tone buzzer BZ1 that emits an audible sound when the mode button 21 and increment button 23 are pressed.

Figure 8A:
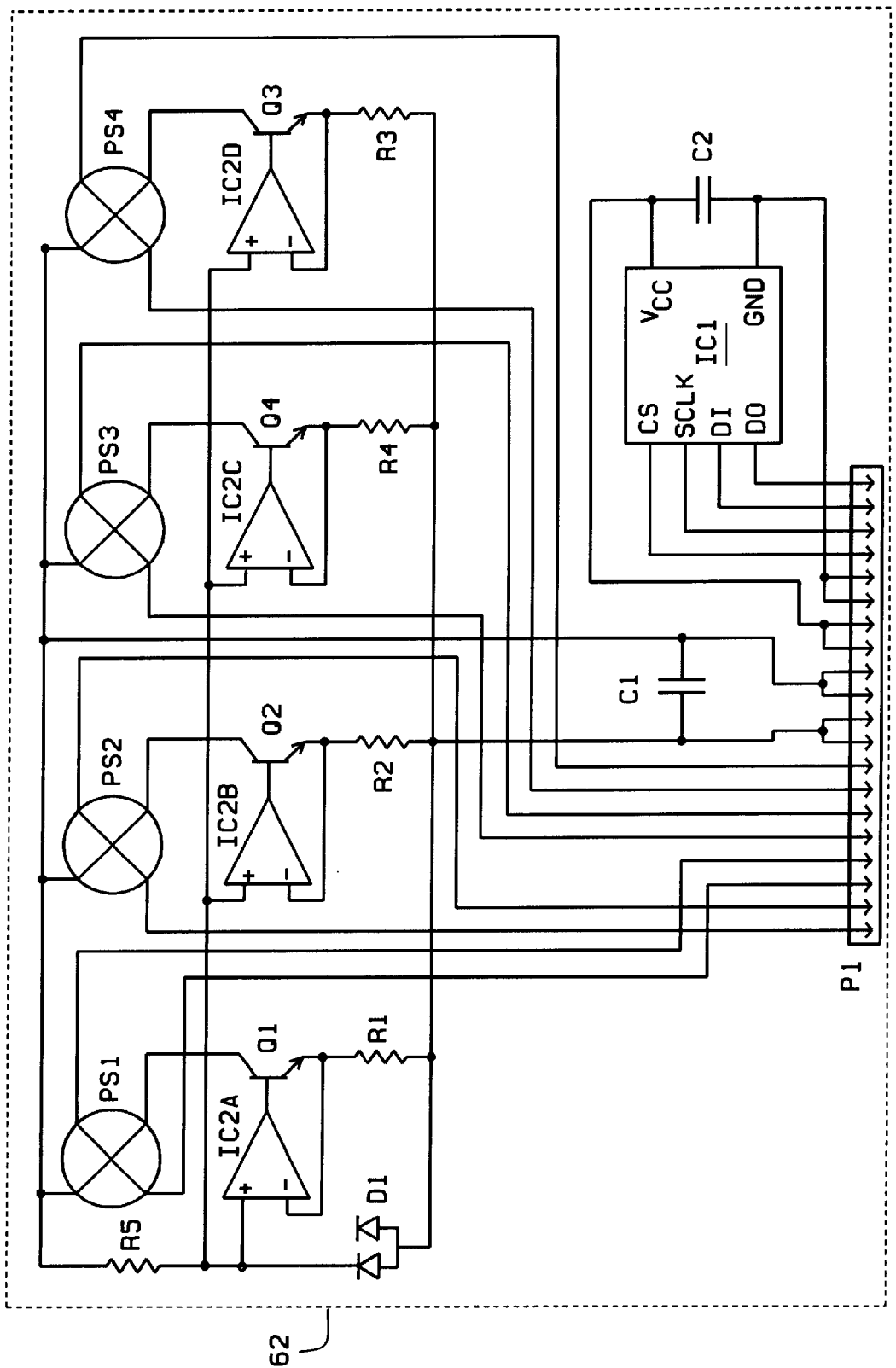
Figure 11:
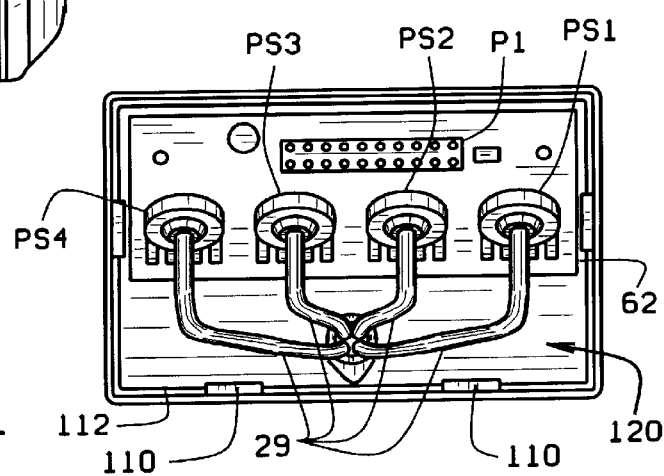
FIG. 11 is a top plan view of the sensor module with the base portion and intermediate portion removed to show the transducers and tube connectors.

In the preferred embodiment, each of the four sensors 40, 46 of the sensor pad 28 are connected to one of four pressure transducers PS1, PS2, PS3 and PS4 disposed on the daughter board 62 in the sensor module 14 via one of the four fluid filled tubes 29 (see FIG. 11). The transducers PS1–PS4 are sold by SenSym of Sunnyvale, Calif., as model number SCC30. One of four operational amplifiers IC2-A, IC2-B, IC2-C and IC2-D is connected to each transducer PS1, PS2, PS3, PS4, respectively, as shown in FIG. 8A, along with associated transistors Q1, Q2, Q4 and Q3 and resistors R1, R2, R4 and R3, respectively. The transistors are sold by Motorola, Inc. of Schaumburg, Ill., under model number 2N3904, and each resistor has a value of 1.62 kΩ. The operational amplifiers IC2A–D and associated components act as constant current sources to drive the corresponding transducers PS1–PS4. In the preferred embodiment, the operational amplifiers IC2A–D are high gain, internally frequency compensated operational amplifiers sold by National Semiconductor Corporation of Santa Clara, Calif. under model number LM324. The transducers PS1–PS4 sense pressures in the tubing 29, and generate analog pressure dependent output voltages representative of the sensed pressures.

It will be appreciated that additional transducers and associated circuitry can be included on the daughter board if more than four sensors are included on the pad 28 or if more than one sensor pad is employed for a particular application.

The circuitry disposed in the sensor module 14 on the daughter board 62 and shown in FIG. 8A further includes a memory device IC1 that is electrically connected to the microprocessor IC4 mounted on the motherboard 62. The memory device IC1 preferably is an electrically erasable programmable read only memory (EEPROM) device that is used to store data, including data relating to the sensors 40, 46 and transducers PS1–PS4. More specifically, the memory device IC1 preferably stores calibration data including calibration curves specific to the associated sensors 40, 46 that is updated each time the apparatus 10 is recalibrated; preprogrammed software correction factor data that compensates for errors that occur as a result of perturbing effects at the interface between two surfaces; and code data that identifies the particular transducers associated with the sensor module 14 and their required calibration date. User-defined data such as the pressure threshold value and the trend period also is stored in the memory device IC1. The user-defined data is not altered unless and until the user changes the values. Furthermore, the data stored in the memory device IC1 is not erased when the apparatus 10 is turned off or when the battery B1 is disconnected. When the apparatus 10 is turned on, the microprocessor IC4 reads data stored in the memory device IC1 to determine the number, type and characteristics of the sensors and transducers connected to the circuitry 26.

By storing such information in the EEPROM device IC1 on the daughter board 62, the sensor module 14 easily can be replaced with any of a plurality of different sensor modules having any of a wide range of sensors connected thereto, depending upon the physical properties being evaluated. For example, if evaluation pressure and temperature properties are desired, the sensor module 14 with pressure sensor pad 28 connected thereto can be connected to the main module 13 to obtain the desired pressure analysis. After pressure data is evaluated, the sensor module 14 can be removed from the main module 13, and a different sensor module (not shown) having at least one temperature transducer mounted therein, and at least one temperature sensor connected thereto can be plugged into the main module 13. A memory storage device such as an EEPROM is included in this sensor module that stores data including information relating to the temperature sensors and temperature transducers. The identifying information stored in the EEPROM is examined by the microprocessor IC4 when the apparatus is turned on, and the microprocessor IC4 executes functions and various modes of operation based upon the type of sensors attached thereto. Thus, the circuitry 26 associated with the main module can process and evaluate data generated by a plurality of different transducers in response to physical variables measured by a plurality of different sensors based upon the biological or biomedical system being evaluated.

Other components mounted on the daughter board 62 and shown in FIG. 8A include a resistor R5 having a value of 2.00 kΩ, diodes D1 sold by Motorola, Inc. as part number BAW56, capacitor C1 having a value of 1 $\mu$F (16V), and capacitor C2 having a value of 0.01 $\mu$F.

The analog output voltage signals generated by the transducers PS1–PS4 are supplied to an analog to digital (A/D) converter IC3 that is mounted on the motherboard 60 and shown. In the preferred embodiment, the A/D converter IC3 is a precision, wide dynamic range analog to digital converter sold by Burr-Brown Research Corp. of Tucson, Ariz., and has a model number ADS1213U. The A/D converter IC3 generates digital output data representative of pressure applied to the sensors 40, 46, and transmits its digital output data to the microprocessor IC4. In the preferred embodiment, the A/D converter IC3 generates a 22 bit digital signal, and transmits the digital signal to the microprocessor IC4 at a rate of three readings per channel per second, where "channel" refers to the path from the sensors 40, 46 to the microprocessor IC4 via the tubing P1, P2, transducers PS1–PS4, A/D converter IC3 and associated electrical connections.

Figure 8B:
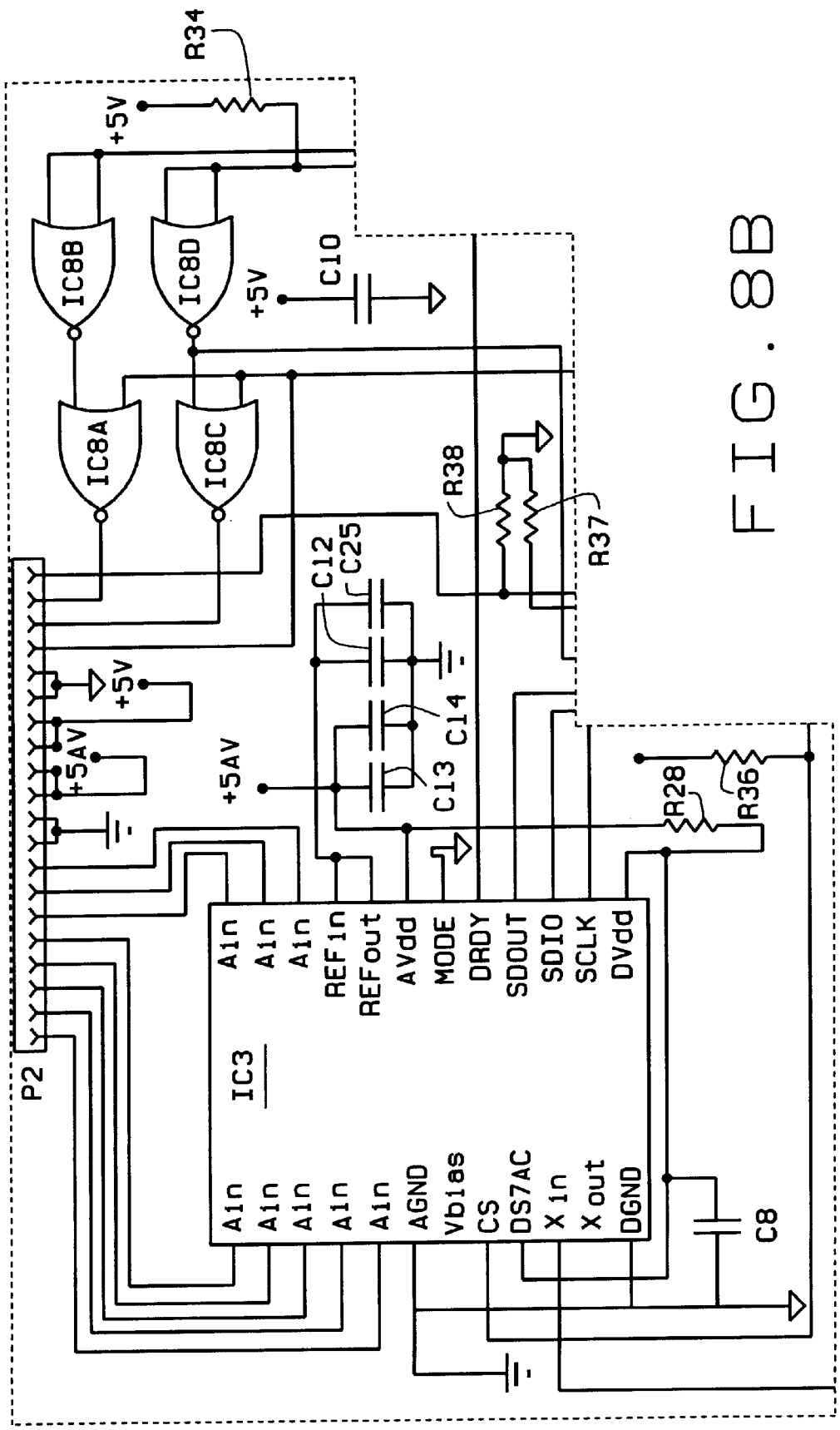

Resistors R37 and R38 are connected to the microprocessor IC4 and the A/D converter IC3, and function as pull down resistors that hold lines in correct polarity when the apparatus is turned on. Resistors R37 and R38 have resistance values of 20 kΩ. Capacitors C13, C14, C12 and C25 are connected to the A/D converter IC3, and are bypass capacitors that filter the power supply, clean out noise from the power supply line and help stabilize the power supply. Capacitors C13 and C25 have values of 0.1 $\mu$F, and capacitors C14 and C12 have values of 1 $\mu$F. As shown in FIG. 8B, other components connected to the A/D converter IC3 include bypass capacitor C8 (0.1 $\mu$F) and resistor R28 (10 Ω).

A set of four NOR gates IC8-A, IC8-B, IC8-C and IC8-D are connected to the EEPROM memory on the daughter board via 20 pin connectors P1 and P2, and perform the function of steering logic for communication between the microprocessor IC4 and the EEPROM IC1. Resistor R34 is connected to the input for NOR gate IC8-D, and has a value of 20 kΩ.

When the digital pressure data is received from the A/D converter IC3 by the microprocessor IC4, the microprocessor IC4 performs a plurality of functions, including processing, storage, output and control functions, to accomplish operations on the data. In the preferred embodiment, the microprocessor IC4 is a 28 pin, 8 bit, 4 MHz microprocessor with 4 megabytes of read-only memory (ROM), 176 bytes of random access memory (RAM) and 20 input/output (I/O) lines that is sold by Motorola, Inc. under the model number MC68HC705P6A. Software programs for controlling operations of the apparatus are stored in the ROM and executed by the microprocessor IC4. A plurality of operations including all calculations, computations, pressure correction and calibration are performed by the microprocessor IC4. Furthermore, audio and visual outputs that are used by the clinician (e.g., via buzzer BZ1, LED bar graph 20 and LCD screen 19) are controlled by the microprocessor IC4. When digital pressure data is received, the microprocessor IC4 calibrates and corrects the data to adjust for any errors in the pressures sensed by the transducers PS-1–PS4 associated with the sensors 40, 46. The microprocessor IC4 then generates output signals representative of the pressure value for the mode requested by the clinician. The push button switches 21, 22, 23 are connected to the microprocessor IC4 via 4-pin connector P3, diodes D4, D5 and resistors R23 (200 kΩ), R26 (20 kΩ), R27 (20 kΩ).

The microprocessor IC4 transmits the output signals to a liquid crystal display (LCD) driver IC12. The LCD driver IC12 preferably is sold by National Semiconductor Corp. under model number MM5453V. The LCD driver IC12 processes the signal received from the microprocessor into a usable format for display on the LCD screen 19. The LCD screen 19 preferably includes a three and one half digit, seven segment display D1, D2 and D3 and a low battery indicator 66.

Other components connected to the LCD driver IC12 include resistor R18 (47 kΩ), capacitor C5 (0.01 $\mu$F) and capacitor C4 (0.01 $\mu$F) that perform the function of a resonator to control the refresh rate of the LCD screen 19. Resistor R41 has a value of 20 kΩ, and is a pull down resistor.

The microprocessor IC4 also transmits output signals to the LEDs LD1–LD20 via a plurality of inverters PA2, PA3, PA4, PA7, PA5, PA6 and associated resistors R40, R6, R7, R8, R9, R10 based upon pressure value for the selected mode of operation. In the preferred embodiment, the inverters PA2–PA7 are Schmitt trigger inverters with built in hysteresis, and sold by Motorola, Inc. under model number 74HC14. Resistors R43, R44, R45, R46 and R47 are 100 kΩ resistors, and resistors R40, R6, R7, R8, R9 and R10 are 200 Ω resistors. The microprocessor IC4 and inverters PA2–PA7 control the energization of the LEDs LD1–LD20 so that those LEDs associated with measured pressure values greater than the threshold pressure value are illuminated in red, and those LEDs associated with measured pressure values equal to or less than the threshold pressure value are illuminated in green. In the preferred embodiment shown in FIG. 8E and discussed above, LEDs LD9–LD17 each include two LEDs that emit differing hues, namely, a red LED R and a green LED G. LEDs LD1–LD8 are red LEDs, and LEDs LD18–LD20 are green LEDs. Transistors Q5, Q6, Q8, Q9 and Q10 and associated resistors R11, R12, R13, R14 and R15 (each having a value of 1.0 kΩ) are connected to the microprocessor and to the LEDs LD1–LD20 as shown in FIG. 8E. In this configuration, transistors Q5, Q6, Q8, Q9 and Q10 are row drivers, and inverters PA2–PA7 act as a column driver in a multiplexing scheme to drive the LEDs LD1–LD20. Resistors R11–R15 are current limiting resistors for the row drivers. The inverters PA2–PA7 provide sufficient current (25 mA) to drive the LEDs.

The circuitry 26 is powered by an on-board 9 volt battery B1 that generates an unregulated direct current (DC) voltage supply UNREG. The output voltage of the battery B1 passes through a diode D3 and three power source filter capacitors C27, C28, C29 connected in parallel, with each capacitor having a value of 470 μF, before being transmitted to other components associated with the circuitry. More specifically, the unregulated voltage generated by the battery B1 is supplied to two micropower voltage regulators IC9 and IC10. In the preferred embodiment, the voltage regulators IC9, IC10 are sold by National Semiconductor Corporation under the model number LP2951. Each voltage regulator IC9, IC10 converts the 9 V DC input voltage into a 5 volt output signal, with regulator IC9 generating 5 V DC, and regulator IC10 generating 5 V DC. Voltage regulator IC9 supplies its 5 V DC output to all digital components associated with the circuitry 26. Voltage regulator IC10 supplies its 5 V DC output to all analog components associated with the circuitry (e.g., the transducers, operational amplifiers and part of the A/D converter IC3. The analog and digital grounds are connected together under the A/D converter IC3 chip. Providing separate power sources for analog and digital sides of the circuit allows for noise reduction. Electronic components associated with voltage regulator IC9 include capacitors C16 (1 μF), C17 (1 μF), and C21 (0.1 μF). Resistor R21 has a value of 20 kΩ. Components associated with voltage regulator IC10 include capacitors C15 (10 μF) and C18 (1 μF).

Diodes D2 and diodes D6 (sold by Motorola, Inc. under model number BAW56), pull-up resistor R22 (20 kΩ), pull-up resistor R24 (20 kΩ), resistor R25 (20 kΩ) and transistor Q7 (sold by Motorola, Inc. under part number 2N3904) are shown in FIG. 8G. Diodes D2 allow power switch 22 to turn on the microprocessor IC4 by isolating input to the microprocessor IC4 from the power switch 22 and allowing current to flow in only one direction from the power switch 22 to the microprocessor IC4. When the power switch is pressed to turn the apparatus on, diodes D2 allow current to flow from the power switch to the microprocessor IC4 to energize the microprocessor. Diodes D6 isolate the power switch 22 from the power transistor Q7 and allow for current flow in only one direction. Thus, diodes D2 and D6 provide necessary power isolation to protect the microprocessor IC4 from excessive voltages associated with the unregulated power supply supplied across resistor R24. Transistor Q7 is a power transistor that holds power onto the voltage regulators IC9 and IC10, and is controlled by the microprocessor IC4.

As shown in FIG. 8G, diodes D4 and D5, sold by Motorola, Inc. as part number BAW56, and associated resistors R26 (20 kΩ) and R27 (20 kΩ) are connected to the mode switch via connector P3. Resistors R26 and R27 are pull-up resistors, and diodes D4 and D5 are part of a multiplexing scheme that allows five inputs on one line of the microprocessor IC4. These diodes D4 and D5 allow the microprocessor to monitor and respond to actuation of the power button 22, mode button 21 and increment button 23. Resistor R23 has a value of 200 kΩ.

Figure 4:
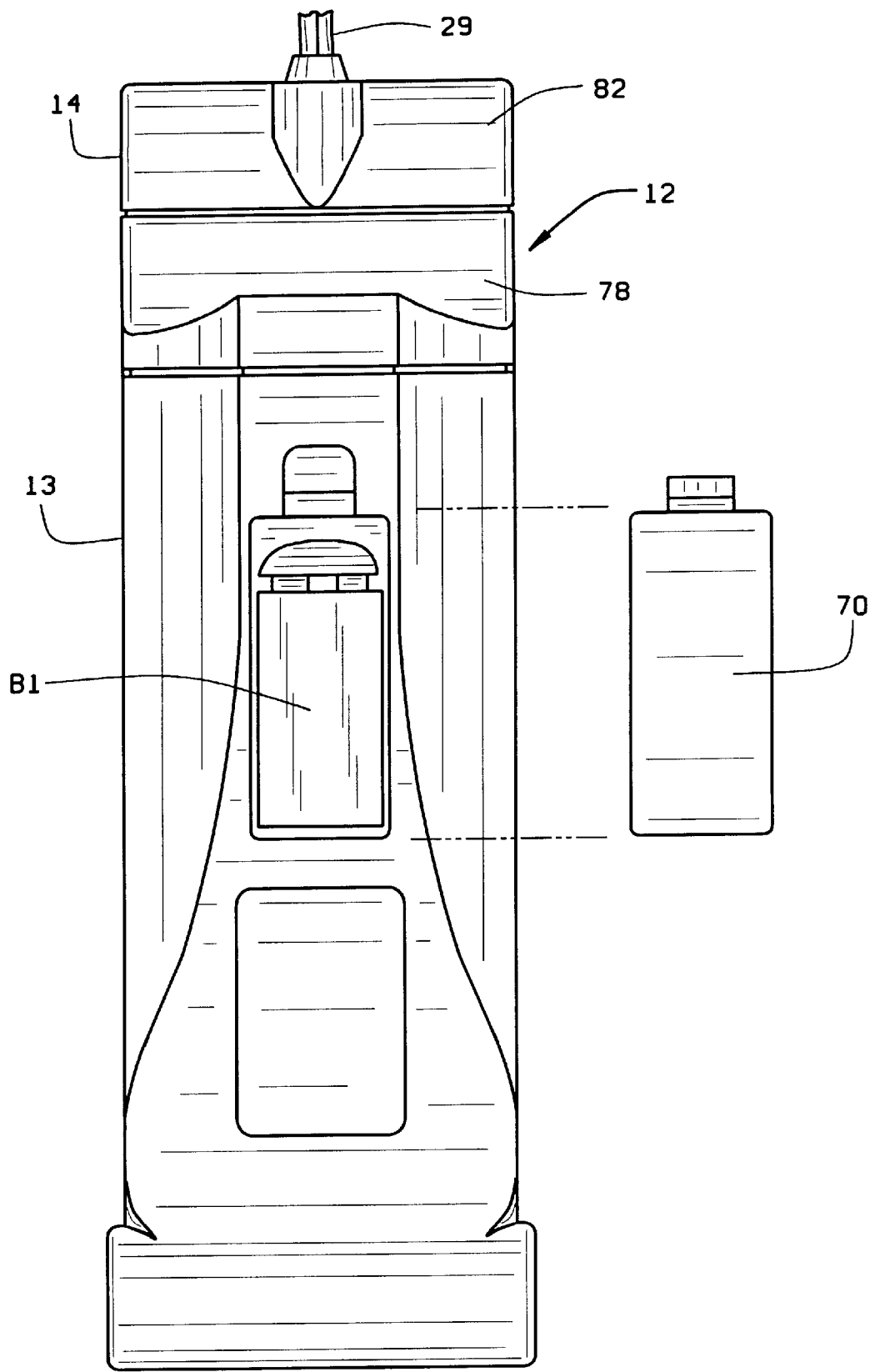
FIG. 4 is a rear elevational view of the hand held unit, showing the battery and removable battery cover.

The 9V battery B1 supplies sufficient power for the device to operate for several weeks or months, depending upon how often it is used. The unregulated voltage generated by the battery B1 is supplied to an undervoltage or low battery detector IC5 (sold by Motorola, Inc. under model number 341664) that detects when the battery B1 power is at or below a set level. In the preferred embodiment, the detector monitors the battery B1 output voltage to determine the output power reaches or falls below a low power output level of 4.5 volts. When this low power output is detected, the detector IC5 generates and transmits a warning signal to the microprocessor IC4, and the microprocessor IC4, in turn, transmits a signal to the LCD driver IC12 so that the LCD driver IC12 causes the low battery indicator 66 to be displayed on the screen 19. The indicator 66 appears on the screen 19 as an initial warning to the clinician that the battery B1 needs to be replaced. To replace the battery B1, a removable battery cover 70 located on the rear of the hand-held unit 12 is removed to access the battery B 1 that is disposed in a cavity 72 formed in the housing 14 (see FIG. 4).

Figure 8C:
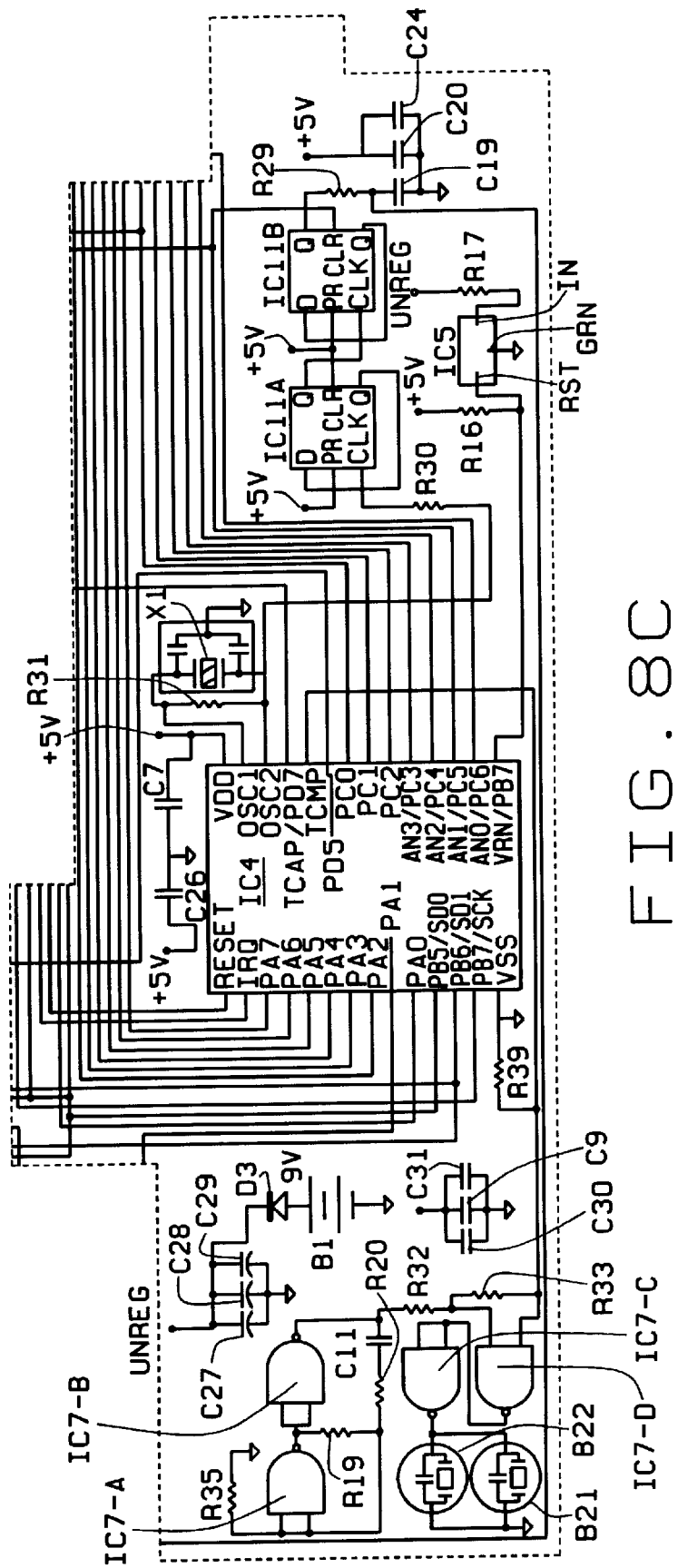
Figure 8D:
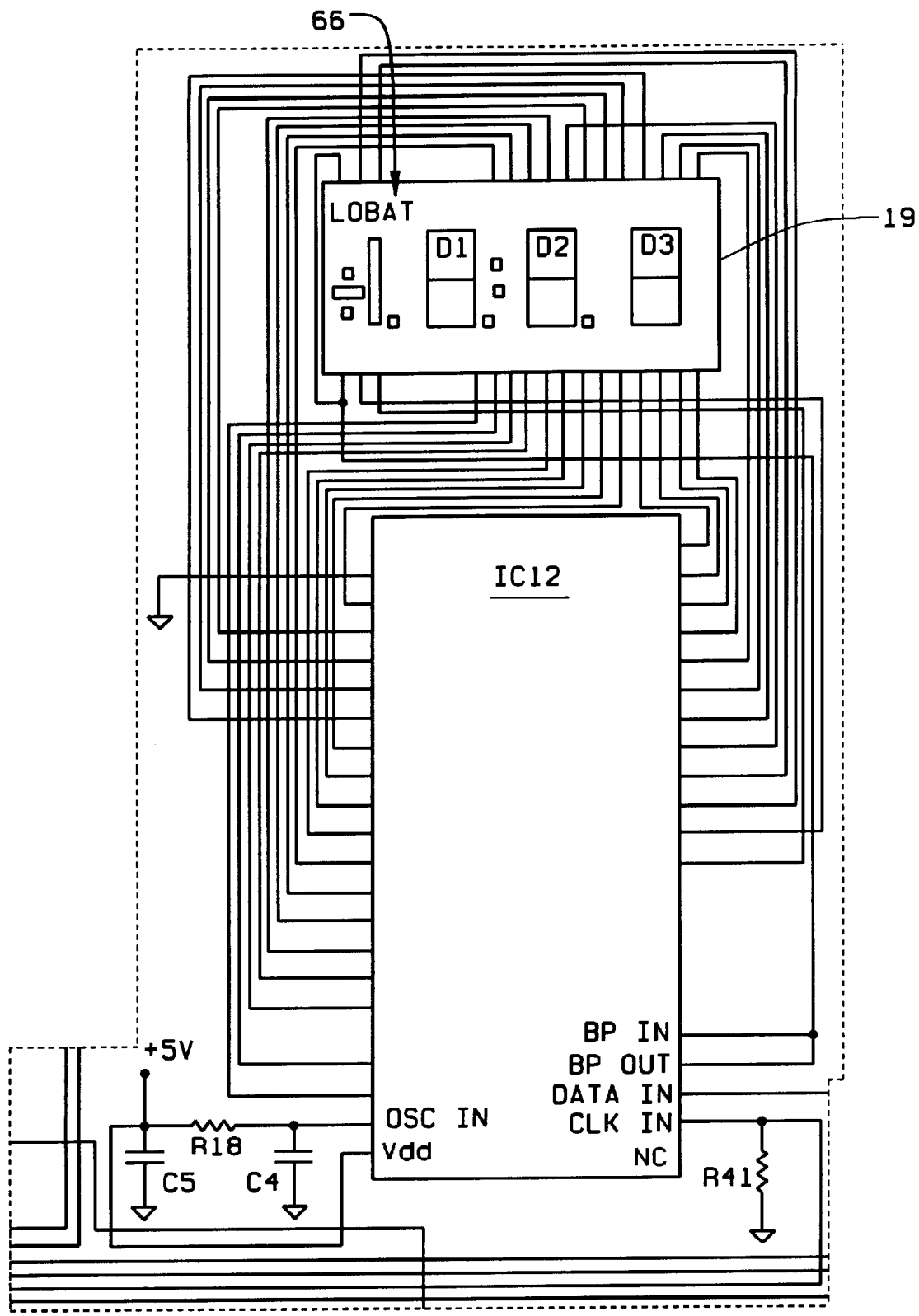
Figure 8E:
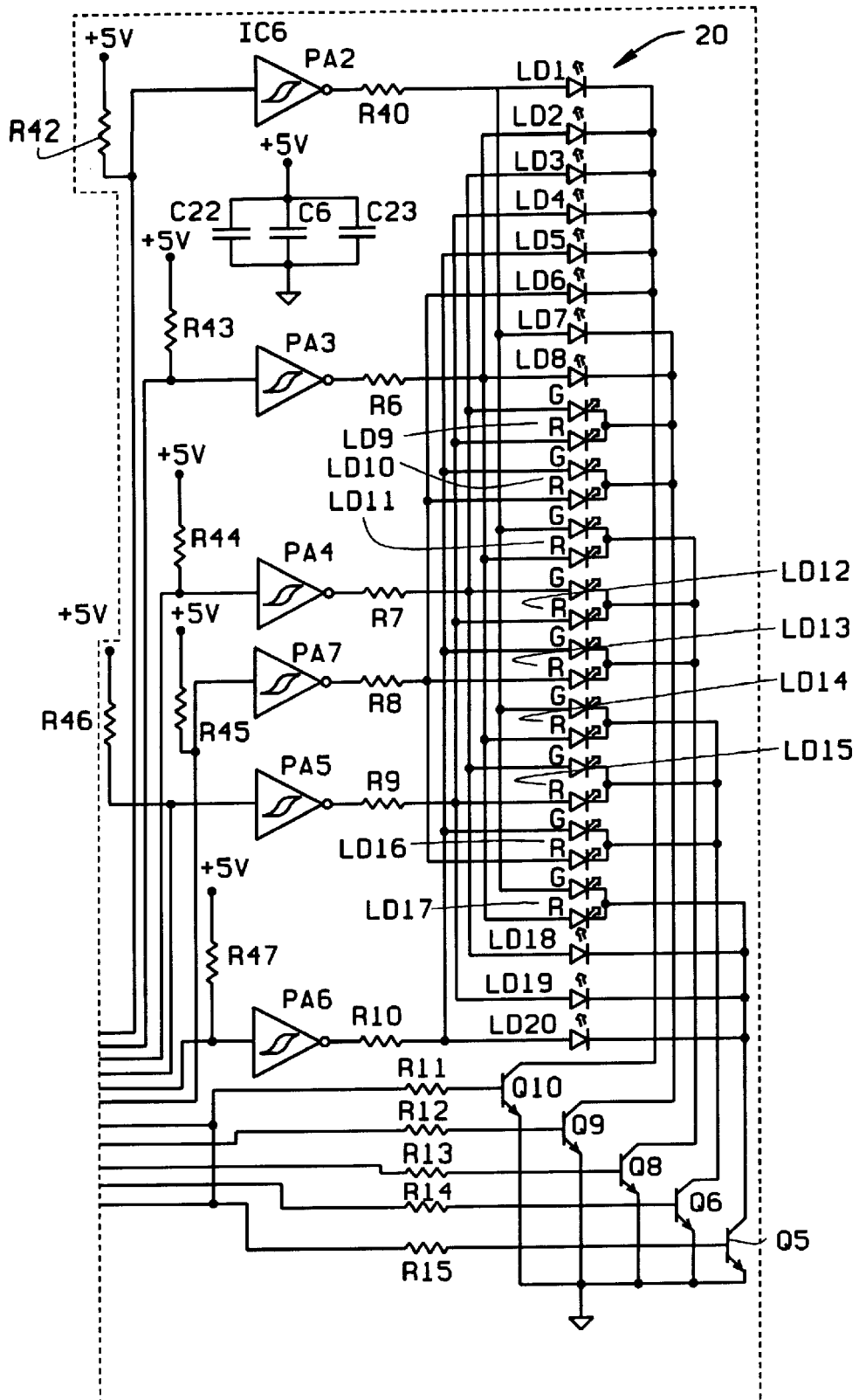

As shown in FIG. 8C, operation of the buzzer BZ1 is controlled by the microprocessor IC4 via NAND gates IC7-A, IC7-B, IC7-C, IC7-D (such as those sold by Motorola, Inc. under part number 74HC00 or by National Semiconductor Corp.), resistors R35 (100 kΩ), R9 (51 kΩ), R20 (3.0 kΩ), R32 (1.0 kΩ) and R33 (1.0 kΩ), and capacitor C11 (2.2 pF). The buzzer BZ1 resonates at 4 kHz. As discussed above, the buzzer BZ1 emits an audible sound (beep) that alerts the clinician when the mode button 21 or increment buttons 23 are pressed. Resistor R39 (100 kΩ) is connected between the microprocessor IC4 and buzzer BZ1, and functions as a pull down resistor so that buzzer BZ1 does not beep during power start when the apparatus 10 is turned on.

Two D flip flops IC11-A and IC11-B and associated components including resistors R29 and R30 and capacitors C19, C20, and C24 are connected to the microprocessor IC4 to divide a clock signal generated by the microprocessor IC4 from 4 MHz to 1 MHz. The 1 MHz signal is supplied to the A/D converter IC3 as a clock signal. Resistors R29 and R30 each have values of 1 kΩ. Capacitor C19 has a value of 150 pF; capacitor C20 has a value of 0.01 μF; and capacitor C24 has a value of 0.1 μF. Other components associated with the microprocessor IC4 include crystal oscillator X1 that resonates at a frequency of 4.00 MHz, and controls the operation of a clock associated with the microprocessor. Resistor R31 has a value of 10 MΩ. Two capacitors C7 (0.01 μF) and C26 (0.1 μF) are connected between the 5 volt supply and a VDD pin of the microprocessor IC4.

Figure 9:
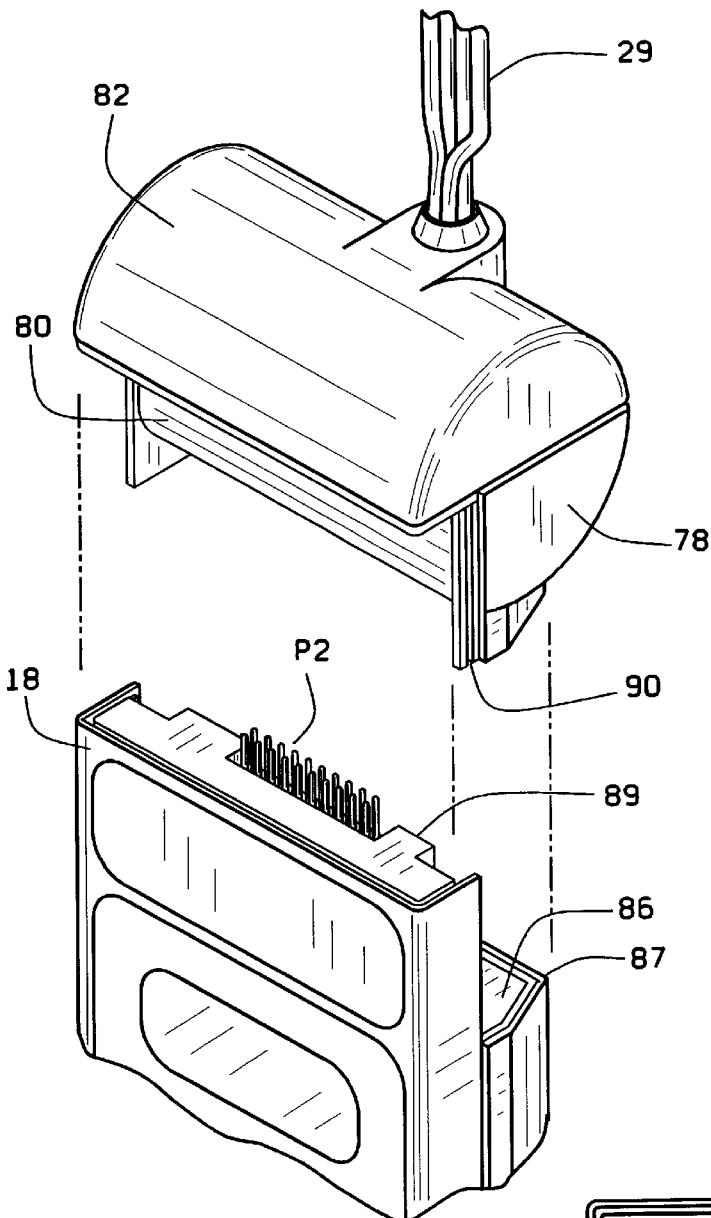
FIG. 9 is a partially exploded perspective view of the hand held unit, showing the sensor module removed from the main module.

FIG. 9 shows a partially exploded view of the hand held unit 12, illustrating the manner in which sensor module 14 is removably secured to the main module 13. The sensor module 14 can be removed when physical properties other than pressure are to be evaluated. For example, if temperature is to be evaluated, the pressure sensor module is removed from the main module 13, and a temperature sensor module (not shown) including at least one temperature transducer that is connected to a temperature sensor is attached to the main module 13 via the pin connector assembly P1 and P2. While the design and configuration of the sensor modules 14 can vary based upon the number of transducers disposed therein and the number and types of sensors attached thereto, each sensor module includes a female pin connector P1 (shown in FIGS. 8 and 11) that is mated with the male pin connector P2 of the main module 13 (shown in FIGS. 8, 9 and 12) to electrically connect the components of the daughter board 62 to the electronic circuitry 26 on the motherboard 60.

This configuration of the sensor module 14 and main module 13 also allows for the sensor module 14 to be easily replaced if the sensors 40 or transducers PS1–PS4 malfunction or become inoperative. FIG. 10 is an exploded view of an illustrative embodiment of housing 76 associated with the sensor module in which the transducers PS1–PS4 and daughter board 62 are disposed. The housing 76 includes a base portion 78, an intermediate portion 80 and a top portion 82. The base portion 78 is removably secured to the main module 13 by a retaining mechanism such as the downwardly extending clip 83 that includes a seat 84 which is inserted inside an opening 85 formed in a first wall 86 of main module housing 88 so that the seat 84 engages the housing 88 (see FIG. 12). The first wall 86 extends substantially perpendicularly between a second wall 89 and a back wall 87 of the main module 13. Applying pressure to the base portion 78 near the clip 83 disengages the seat 80 from the housing 88 to allow the sensor module 14 to be removed from the main module 13.

Figure 10:
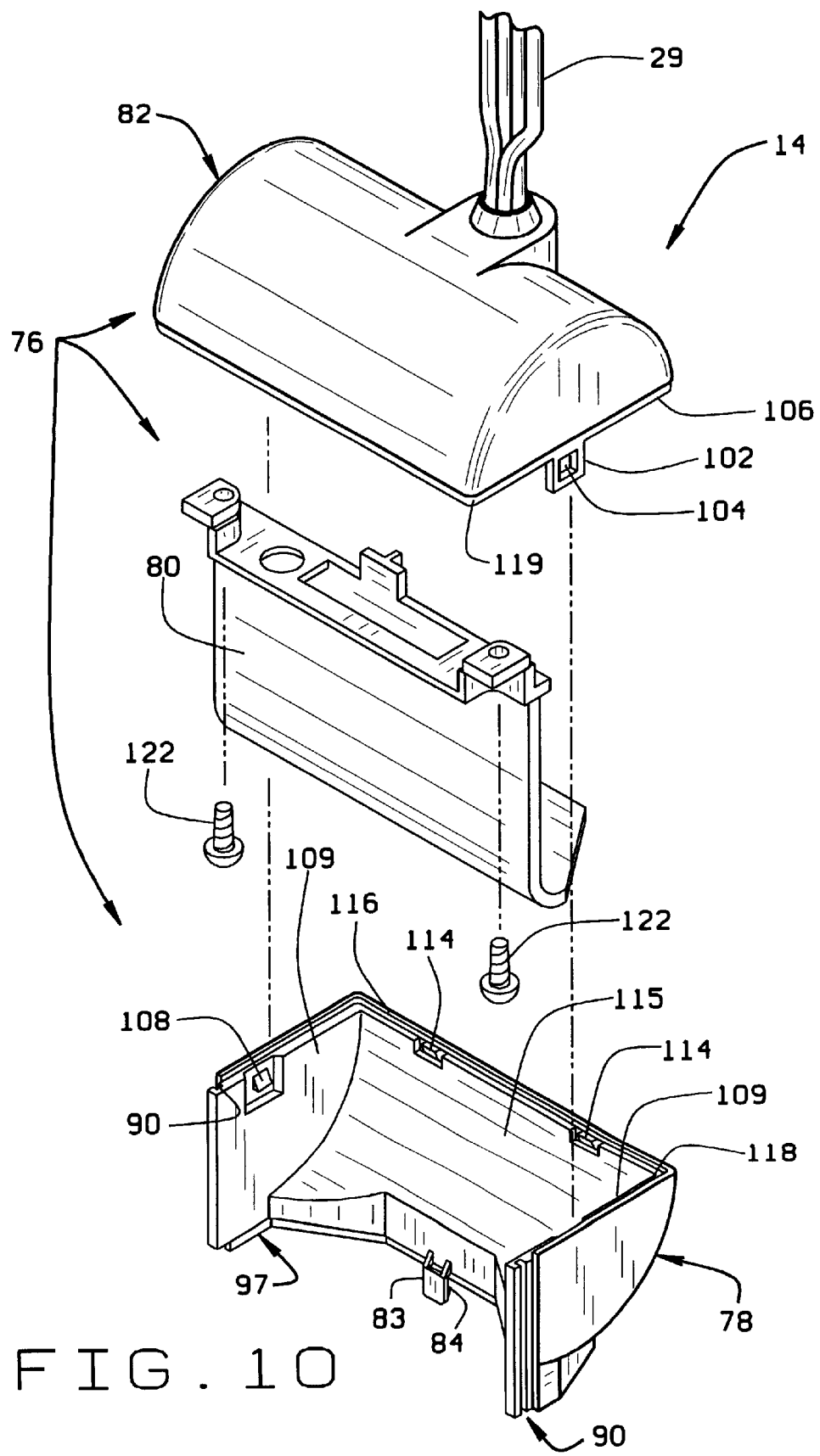
FIG. 10 is an exploded perspective view of the sensor module housing.
Figure 12:
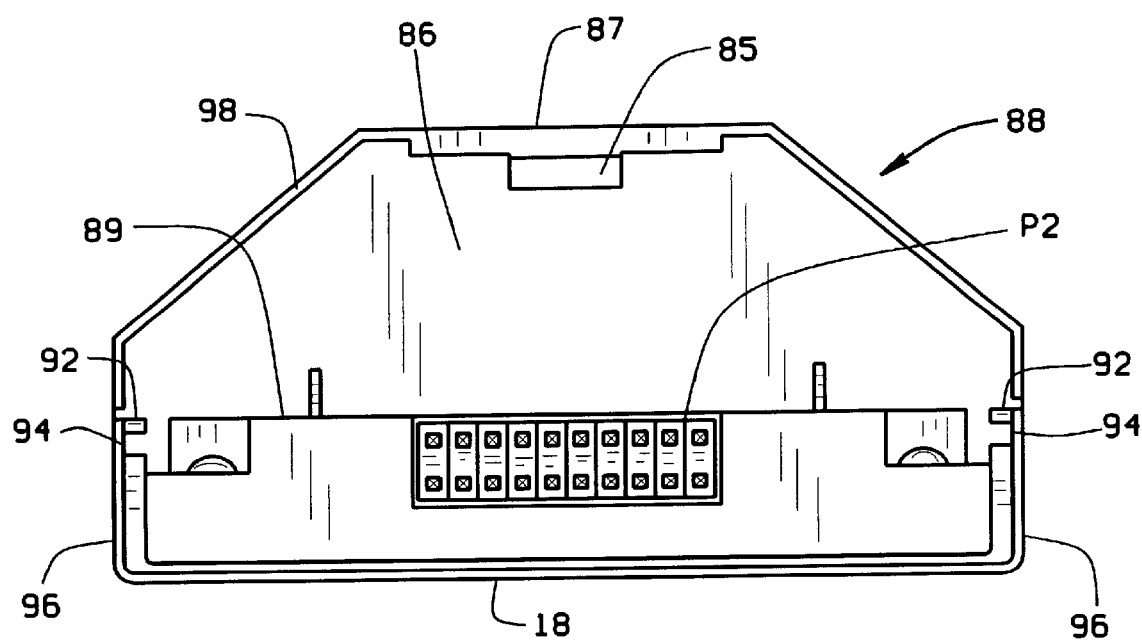
FIG. 12 is a top plan view of the main module.

As shown in FIGS. 10 and 12, the base portion 78 includes two grooved edges 90 that are adapted to be slidingly engaged by protrusions 92 and recesses 94 formed in side walls 96 of the housing 88. The grooves 90, protrusions 92 and recesses 94 further assist in securing the base portion 78 of the sensor module 14 to the main module 13. A lower edge 97 of the base portion defines a seat that snugly engages a shoulder 98 formed at the upper edge of the back of the housing 88 for the main module 13.

The base portion 78 of the sensor module 14 is removably secured to the top portion 82 by retaining mechanisms that allow the base portion to be removed from the top portion 82 to expose the transducers PS1–PS4 so the transducers can be visually inspected for damage if the apparatus 10 is not operating properly. The retaining mechanisms shown in FIG. 10 include a pair of flanges 102 having openings 104 formed therethrough that project downwardly from side edges 106 of the top portion 82. A pair of inwardly extending protrusions 108 are formed on inner side walls 109 of the base portion 78 that are adapted to engage the flanges 102 and be disposed inside the openings 104 when the top portion 82 is positioned on the base portion 78. As shown in FIG. 11, a pair of flanges 110 having openings (not shown) formed therethrough extend downwardly from a back edge 112 of the top portion 82. As shown in FIG. 10, the base portion 78 includes a pair of projections 114 extending inwardly from an inner back surface 115 of the base portion 78 that are adapted to engage the flanges 110 and be disposed inside the openings when the top portion 82 is positioned on the base portion 78. The base portion 78 further includes a seat 116 that is formed at its top edge 118 that is adapted to accommodate a lower edge 119 of top portion 82 and restrict movement of the top portion 82 with respect to the base portion 78.

The daughter board 62 is disposed inside a recess 120 formed in the top portion 82 of the sensor module 62, and the transducers PS1–PS4 are connected thereto. To protect the components on the daughter board 62 and further strengthen the housing 76, the intermediate portion 80 is attached to the daughter board 62 and top portion 82 by fasteners such as screws 122. As shown in FIG. 9, the intermediate portion 80 blocks access to the transducers PS1–PS4 and protects connections between the transducers PS1–PS4 and tubing 29 when the sensor module 13 is removed from the main module 14. The intermediate portion 80 allows for quick visual inspection the transducers upon removal of the base portion 78 to detect potential problems if the apparatus 10 is not operating properly. The intermediate portion 80 can be removed easily from the top portion 82 to expose the transducers PS1–PS4 and daughter board 62 (FIG. 11) by removing the screws 122. This configuration of the sensor module 14 also allows for any of the sensor pad 28, transducers PS1–PS4 and daughter board 62 to be repaired or replaced to correct problems if the apparatus 10 malfunctions.

It will be appreciated that the main module 13 is configured to readily accommodate sensor modules of various construction and configurations. Thus, the dimensions of sensor module 14 can be changed to accommodate more or less transducers as needed for a particular application. Furthermore, the sensor module 14 construction can be altered to accommodate transducers of varying sizes and dimensions based upon the types of sensors employed. Moreover, the pin assembly P1, P2 allows for connection of one or more sensor pads to the hand-held unit 12.

In view of the above, it will be seen that the several objects and advantages of the present invention have been achieved and other advantageous results have been obtained.

The foregoing description is set forth only for illustrative purposes only and is not meant to be limiting. As various changes could be made in the above constructions without departing from the scope of the invention, it is intended that all matter contained in the above description or shown in the accompanying drawings shall be interpreted as illustrative and not in a limiting sense. Numerous variations, within the scope of the appended claims will be apparent to those skilled in the art in light of the foregoing description and accompanying drawings.

What is claimed is:

1. A hand-held biomedical apparatus for monitoring and evaluating physical properties associated with a biological system, comprising:

a sensor module including at least one sensor for measuring physical variables associated with the biological system, and generating data representative of measured variables;

at least one transducer in communication with said sensor for generating output signals representative of physical variables measured by the sensor;

data processing circuitry electrically connected to said transducer for processing output signals generated by the transducer and generating data based upon physical properties measured by the sensor;

a display electrically connected to the data processing circuitry for visually displaying information representative of physical property data generated by the data processing circuitry;

a hand-held housing in which said transducer and said data processing circuitry are disposed, and on which said display is disposed;

at least one connector extending between the sensor module and the housing for removably connecting said sensor module to said transducer; and a power source disposed inside said housing for supplying power to said apparatus.

2. A biomedical apparatus for monitoring and evaluating pressure at any interface between two abutting surfaces, comprising:

a sensor pad including at least one sensor that is adapted to be disposed between the two surfaces to measure pressures exerted on one surface by the other surface, and generate data representative of measured pressures; said pad having a sensor end and a connection end at least one transducer, said at least one transducer being in communication with each sensor for generating output signals representative of pressures measured by the sensor;

data processing circuitry electrically connected to said at least one transducer for processing output signals generated by the transducer and generating pressure data based upon pressures measured by the sensor;

a display electrically connected to the data processing circuitry for visually displaying information representative of pressure data generated by the data processing circuitry;

a hand-held housing removably attached to said sensor pad at the connection end thereof, said hand-held housing containing said at least one transducer, said data processing circuitry and said display;

tubing extending between the sensor pad and the housing for connecting each sensor to one transducer and being operatively connected to the sensor pad along the connection end thereof; and a power source disposed inside said housing for supplying power to said apparatus.

3. The biomedical apparatus as set forth in claim 2 wherein said sensor pad includes at least three sensors, with each sensor being in communication with one transducer.

4. The biomedical apparatus as set forth in claim 2 wherein said sensors are disposed in a matrix configuration.

5. The biomedical apparatus as set forth in claim 2 wherein said sensors are arranged to provide a surface area that covers a bony prominence of an individual.

6. The biomedical apparatus as set forth in claim 2 wherein said sensors are fluid-filled, hydraulic sensors.

7. The biomedical apparatus as set forth in claim 6 wherein said sensors have a quadfoliate configuration.

8. The biomedical apparatus as set forth in claim 6 wherein said tubing includes a plurality of fluid filled tubes with each sensor being connected to one transducer by one of said tubes.

9. The biomedical apparatus as set forth in claim 8 wherein the fluid contained in said sensors is a hydrogenated synthetic hydrocarbon base fluid.

10. The biomedical apparatus as set forth in claim 8 wherein said sensor pad further includes a reference sensor, said reference sensor being connected to a transducer by a fluid filled tube, said reference sensor measuring hydrostatic forces that may exist in the fluids contained inside its tube, said transducer generating an output signal representative of hydrostatic forces measured by said reference sensor that is processed by said data processing circuitry, said data processing circuitry generating pressure data that is adjusted to compensate for hydrostatic forces.

11. The biomedical apparatus as set forth in claim 2 wherein said data processing circuitry includes a microprocessor that performs input, processing, storage, output and control functions on data generated by the sensors.

12. A portable biomedical apparatus for monitoring and evaluating pressures exerted on an individual by a surface against which at least a portion of the individual's body rests, comprising:

one or more sensor pads with each sensor pad having at least three pressure sensors, and being adapted to be disposed between he individual's body and the surface to measure pressures exerted on the individual's body by the surface, and generating data representative of measured pressures;

a plurality of transducers in communication with said sensors for generating output signals representative of pressures measured by the sensors;

electronic circuitry electrically connected to said transducers including a microprocessor operatively connected to said transducers for performing a plurality of functions on the output signals generated by the one or more sensor pads;

a hand-held housing in which said transducers and said electronic circuitry are disposed;

a display assembly electrically connected to said microprocessor for displaying pressure information based upon output data generated by said microprocessor, said display being visible on said housing;

tubing extending between the sensor pad and the housing for connecting the sensors to the transducers;

a power switch mounted on said housing and electrically connected to said electronic circuitry for selectively turning said apparatus off and on by interrupting the supply of power from a power supply to the electronic circuitry;

a power source disposed inside said housing for supplying power to the electronic circuitry, said microprocessor executing a self-calibration function when the power switch is pressed for a predetermined time interval to calibrate the sensor properly prior to measuring pressures exerted by the surface on the individual's body.

13. The pressure measurement apparatus as set forth in claim 12 further including a mode push-button switch mounted on said housing and electrically connected to said microprocessor, said mode switch being manually actuated by an operator of said apparatus to selectively control execution of subsequent functions performed by said microprocessor that are associated with one of a plurality of modes of operation, said microprocessor cycling through the modes of operation when the mode switch is pressed.

14. The biomedical apparatus as set forth in claim 13 wherein the modes of operation of said microprocessor include a maximum pressure mode in which said microprocessor compares pressures measured by each of the pressure sensors and determines a maximum pressure measured by any of said sensors, said display displaying maximum pressure information when said microprocessor is in the maximum pressure mode based upon data generated by said microprocessor.

15. The biomedical apparatus as set forth in claim 14 wherein the modes of operation of said microprocessor further includes an average pressure mode in which said microprocessor determines an average pressure measured by all pressure sensors, said display displaying average pressure information when said microprocessor is in the average pressure mode based upon data generated by said microprocessor.

16. The biomedical apparatus as set forth in claim 15 wherein the modes of operation of said microprocessor further includes a maximum pressure trend mode in which said microprocessor determines maximum pressures measured by any of said sensors over a predefined period of time, and an average pressure trend mode in which said microprocessor determines average pressures measured by the sensors over the predefined period of time, said display displaying continuously updated maximum pressure information when said microprocessor is in the maximum pressure trend mode based upon data generated by said microprocessor, said display displaying continuously updated average pressure information when said microprocessor is in the average pressure trend mode based upon data generated by said microprocessor.

17. The biomedical apparatus as set forth in claim 15 wherein the modes of operation of said microprocessor further include a pressure index mode in which said microprocessor determines a pressure index based upon the difference between the maximum pressure and the average pressure.

18. The biomedical apparatus as set forth in claim 16 further including an increment push-button switch that is mounted on said housing and electrically connected to said microprocessor, said increment switch being manually actuated by the operator of the apparatus to selectively control execution of functions by said microprocessor associated with said modes of operation.

19. The biomedical apparatus as set forth in claim 18 wherein said increment switch is pressed to toggle between the maximum pressure mode and the average pressure mode, and to toggle between the maximum pressure trend mode and the average pressure trend mode.

20. The biomedical apparatus as set forth in claim 18 wherein said modes of operation further includes a set time period mode in which the time interval over which average pressures are calculated during the average pressure trend mode and maximum pressures are calculated during the maximum pressure trend mode is defined.

21. The biomedical apparatus as set forth in claim 20 wherein said increment switch is manually actuated by the operator when said microprocessor is in the set time period mode to selectively adjust and define the time period over which average pressures are calculated during the average pressure trend mode and maximum pressures are calculated during the maximum pressure trend mode.

22. The biomedical apparatus as set forth in claim 18 wherein said modes of operation further includes a set units of measurement mode in which units of pressure for pressure information displayed on the display are defined as either mmHg or kPa.

23. The biomedical apparatus as set forth in claim 22 wherein said increment switch is manually actuated by the operator when said microprocessor is in the set units of measurement mode to select either mmHg or kPa as the units of pressure for pressure information displayed on the display.

24. The biomedical apparatus as set forth in claim 18 wherein said modes of operation further includes a threshold adjustment mode in which a desired maximum pressure value is adjusted and defined within a preprogrammed range of pressure values, said increment switch being manually actuated by the operator when said microprocessor is in the threshold adjustment mode to select a desired threshold pressure value.

25. The biomedical apparatus as set forth in claim 12, wherein said display shows information indicating said microprocessor is performing the self-calibration function during execution of the self-calibration function, and shows information indicating the self-calibration function is completed by the microprocessor.

26. The biomedical apparatus as set forth in claim 25, wherein said display includes a liquid crystal display (LCD) screen.

27. The biomedical apparatus as set forth in claim 26, wherein the microprocessor causes the LCD screen to display one of a plurality of alphanumeric symbols based upon the current mode of operation of the microprocessor, with a different symbol being associated with each mode of operation.

28. The biomedical apparatus as set forth in claim 12, wherein said display includes a light emitting diode (LED) bar graph display, said bar graph display including a plurality of pressure values labeled on the housing for a range of pressures and a plurality of LEDs extending outwardly through an opening formed in said housing, at least one LED being disposed in close proximity to each labeled pressure value, said LEDs being electrically connected to said microprocessor, said microprocessor triggering energization of at least a portion of said LEDs based upon pressure data generated by the microprocessor.

29. The biomedical apparatus as set forth in claim 13, wherein said modes of operation include a threshold adjustment mode in which a desired maximum pressure value is adjusted and defined within a preprogrammed range of pressure values, and wherein said display includes a light emitting diode (LED) bar graph display having a plurality of LEDs with at least one LED being associated with each of a plurality of pressure values labeled on the housing, said circuitry controlling illumination of said LEDs based upon pressure data generated by said microprocessor, said circuitry illuminating LEDs associated with pressure values that exceed the desired maximum pressure in a first hue, and illuminating LEDs associated with pressure values less than or equal to the desired maximum pressure in a second hue.

30. The biomedical apparatus as set forth in claim 12, wherein said electronic circuitry further includes a low power detector that monitors power supplied by the power source, and generates a warning signal when the power level fails below a specified level, said low power detector being electrically connected to said microprocessor, said microprocessor causing said display to show a low power indicator symbol when said low power detector generates the warning signal.

31. The biomedical apparatus as set forth in claim 12, wherein said sensors are hydraulic sensors.

32. The biomedical apparatus as set forth in claim 31, wherein said sensors have a quadfoliate configuration.

33. The biomedical apparatus as set forth in claim 31, wherein said tubing includes a plurality of fluid filled tubes with each sensor being connected to one transducer by one of said tubes.

34. The biomedical apparatus as set forth in claim 33, wherein the fluid contained in said sensors is a hydrogenated synthetic hydrocarbon based fluid.

35. The biomedical apparatus as set forth in claim 33, wherein said sensor pad further includes a reference sensor, said reference sensor being connected to a transducer associated with said electronic circuitry by tubing, said reference sensor measuring hydrostatic forces that may exist in the fluids contained inside its tubing, said transducer generating an output signal representative of hydrostatic forces measured by said reference sensor that is processed by said microprocessor, said microprocessor adjusting output data to compensate for hydrostatic forces.

36. A biomedical apparatus for monitoring and evaluating pressure at any interface between two abutting surfaces, comprising:

one or more sensor pads with each sensor pad including one or more hydraulic pressure sensors and a hydraulic reference sensor, each sensor pad being adapted to be disposed between the two surfaces to measure pressures exerted on one surface by the other surface, and generate data representative of measured pressures;

at least two transducers with one transducer being in communication with each pressure sensor and the reference sensor for generating output signals representative of pressures measured by the sensors;

data processing circuitry electrically connected to said transducers for processing output signals generated by the transducers and generating pressure data based upon pressures measured by the sensors;

a display assembly electrically connected to the data processing circuitry for visually displaying representative of pressure data generated by the data processing circuitry;

a hand-held housing in which said transducers and data processing circuitry are disposed, and on which said display is disposed;

a power source disposed inside said housing for supplying power to said apparatus; and at least two fluid filled tubes extending between the sensor pad and the housing for connecting each sensor to one transducer, said reference sensor measuring hydrostatic forces that may exist in the fluids contained inside its tube, said transducer connected to said reference sensor generating output signals representative of hydrostatic forces measured by said reference sensor that are processed by said data processing circuitry, said data processing circuitry generating pressure data that is adjusted to compensate for hydrostatic forces.

37. The biomedical apparatus as set forth in claim 36, wherein the fluid contained in said cells is a hydrogenated synthetic hydrocarbon base fluid.

38. The biomedical apparatus as set forth in claim 36, wherein each sensor has a quadfoliate configuration.

39. A biomedical apparatus for monitoring and evaluating physical properties associated with a biologic system, comprising:

a main module including a housing having a cavity formed therein, data processing circuitry disposed in the cavity of the main module housing, and a display assembly electrically connected to said data processing circuitry;

a sensor module removably secured to said main module including a housing having a cavity formed therein, at least one transducer disposed in the sensor module housing, and a memory device disposed in the sensor module housing, said transducer being electrically connected to said data processing circuitry when said sensor module is secured to said main module; and at least one sensor for measuring physical variables associated with the biologic system and generating data representative of measured variables, said sensor being in communication with said transducer, whereby said transducer generates output signals representative of physical variables measured by the sensor, said data processing circuitry processes output signals generated by the transducer and generates data based upon based upon physical properties measured by the sensor, and said display assembly displaying information based upon data generated by said data processing means.

40. The biomedical apparatus as set forth in claim 39, further including a memory device disposed in the sensor module housing and electrically connected to said data processing circuitry, said memory device having data stored therein representative of characteristics associated with said sensor and said transducer, said data processing circuitry examining data stored in said memory device to determine characteristics associated with the sensor and transducer.

41. The biomedical apparatus as set forth in claim 39, wherein physical properties measured by said sensor include pressure.

42. The biomedical apparatus as set forth in claim 39, wherein physical properties measured by said sensor include partial pressure oxygen.

43. The biomedical apparatus as set forth in claim 39, wherein physical properties measured by said sensor include carbon dioxide.

44. The biomedical apparatus as set forth in claim 39, wherein physical properties measured by said sensor include humidity.

45. The biomedical apparatus as set forth in claim 39, wherein physical properties measured by said sensor include friction.

46. The biomedical apparatus as set forth in claim 39, wherein physical properties measured by said sensor include force.

47. The biomedical apparatus as set forth in claim 39, wherein physical properties measured by said sensor include linear and angular displacement.

48. The biomedical apparatus as set forth in claim 39, wherein physical properties measured by said sensor include radiant energy.

49. The biomedical apparatus as set forth in claim 39, wherein physical properties measured by said sensor include blood flow.

50. The biomedical apparatus as set forth in claim 39, wherein physical properties measured by said sensor include temperature.

51. A biomedical apparatus for monitoring and evaluating pressure at an interface between two surfaces, comprising:

at least one sensor adapted to be disposed between the two surfaces to measure pressures exerted on one surface by the other surface, and generate data representative of measure pressures;

a hand-held housing having a sensor module removably mounted to it, said sensor module including at least one transducer in communication with said sensor for generating output signals representative of pressures measured by the sensor; and a main module in said housing, said main module being removably secured to said sensor module, said main module including data processing circuitry electrically connected to said transducer for processing output signals generated by the transducer and generating data based upon pressures measure by the sensor, and a display electrically connected to said data processing circuitry for visually displaying information representative of pressure data generated by the data processing circuitry.

52. A sensor pad for measuring pressures at an interface between two surfaces, comprising at least one hydraulic sensor having a quadfoliate configuration.

53. The sensor pad as set forth in claim 52 including at least three hydraulic sensors disposed in a matrix configuration to provide a surface area that covers a bony prominence of an individual.

54. The sensor pad as set forth in claim 52 wherein the sensor is a fluid-filled cell having a hydrogenated synthetic hydrocarbon base fluid disposed in the cell.

55. A method for evaluating pressure exerted on a first surface by a second surface comprising the steps of:

measuring pressures exerted on the first surface by the second surface at two or more different locations;

comparing pressures measured at the different locations to determine a maximum measured pressure;

comparing pressures measured at the different locations to determine an average measured pressure; and determining a pressure index based upon the difference between the maximum measured pressure and the average measured pressure.

56. The method as set forth in claim 55 further including the steps of:

determining a maximum pressure trend based upon maximum measured pressures over a predefined period of time, and determining an average pressure trend based upon average measured pressures over the predefined period of time.

57. A method of detecting likely development of body sores on a patient comprising:

positioning a plurality of sensors at locations likely to develop body sores at an interface between two surfaces;

generating data from the sensors;

correlating the data generated; and determining a patient movement strategy based on the correlated data;

wherein said sensors measure one or more physical variables selected from the group comprising: pressure, temperature, partial pressure oxygen, carbon dioxide, humidity, friction, force, displacement, radiant energy and blood flow.

* * * * *